(12) United States Patent
Compton et al.

(10) Patent No.: US 11,850,556 B2
(45) Date of Patent: Dec. 26, 2023

(54) FRIT FOR USE WITH MOLECULAR WEIGHT FILTRATION SYSTEM AND APPARATUS

(71) Applicant: Integrated Protein Technologies, Inc., Evanston, IL (US)

(72) Inventors: Philip D. Compton, Chicago, IL (US); Jared Drader, San Marcos, CA (US)

(73) Assignee: Integrated Protein Technologies, Inc., Evanston, IL (US)

( * ) Notice: Subject to any disclaimer, the term of this patent is extended or adjusted under 35 U.S.C. 154(b) by 632 days.

(21) Appl. No.: 17/096,146

(22) Filed: Nov. 12, 2020

(65) Prior Publication Data

US 2021/0060496 A1 Mar. 4, 2021

Related U.S. Application Data

(63) Continuation-in-part of application No. 16/193,539, filed on Nov. 16, 2018, now Pat. No. 10,864,483.

(51) Int. Cl.
*B01D 69/10* (2006.01)
*B01D 63/08* (2006.01)

(52) U.S. Cl.
CPC .............. *B01D 69/10* (2013.01); *B01D 63/08* (2013.01); *B01D 2313/04* (2013.01); *B01D 2313/12* (2013.01); *B01D 2313/20* (2013.01)

(58) Field of Classification Search
CPC ............ B01D 2313/04; B01D 2313/20; B01D 2313/50; B01D 63/087; B01D 2313/025; B01D 2313/08; B01D 2313/10; B01D 2313/12; B01D 2313/13; B01D 2313/54; B01D 2313/56; B01D 2313/58; B01D 2317/02; B01D 2317/08; B01D 2325/20; B01D 2325/34; B01D 61/14; B01D 61/145; B01D 63/08; B01D 63/082; B01D 63/088; B01D 69/02; B01D 69/10
See application file for complete search history.

(56) References Cited

U.S. PATENT DOCUMENTS

| | | | |
|---|---|---|---|
| 2,650,670 A * | 9/1953 | Cichelli | B01D 53/22 261/114.5 |
| 4,222,874 A * | 9/1980 | Connelly | B01D 61/02 210/652 |
| 10,864,483 B2 * | 12/2020 | Compton | B01D 69/02 |
| 2004/0219072 A1 * | 11/2004 | Yamakawa | B01L 3/502753 422/400 |
| 2018/0104650 A1 * | 4/2018 | Kamito | B01D 63/087 |
| 2022/0193616 A1 * | 6/2022 | Compton | C12N 15/1017 |

* cited by examiner

*Primary Examiner* — Andre J Allen
(74) *Attorney, Agent, or Firm* — Kevin Schraven; Anooj Patel; Hankin Patent Law, APC

(57) ABSTRACT

A frit comprising a plurality of grooves; a drain hole; a transverse crossing lane; wherein said plurality of grooves are substantially parallel to one another and extend longitudinally across said frit; wherein said plurality of grooves comprise at least two different lengths; wherein said transverse crossing lane is substantially perpendicular to said plurality of grooves; wherein said drain hole is located within said transverse crossing lane; wherein said drain hole is located at a center of said transverse crossing lane.

18 Claims, 23 Drawing Sheets

FRIT FOR USE WITH MOLECULAR WEIGHT FILTRATION SYSTEM AND APPARATUS

CROSS-REFERENCE TO RELATED APPLICATION

This application is a Continuation-In-Part of U.S. Non-Provisional application Ser. No. 16/193,539, now U.S. Pat. No. 10,864,483, filed on Nov. 16, 2018, entitled "MOLECULAR WEIGHT FILTRATION SYSTEM AND APPARATUS", the contents of which are incorporated herein by reference as thought set forth in their entirety.

FIELD OF USE

This disclosure pertains to a frit for use with a system and apparatus for filtration, purification, and concentration of biological molecules based on the molecules' molecular weight cut-off. More particularly, the frit may comprise a grooved frit configured to support a membrane used in a system for proteomics sample preparation, wherein the sample size is extremely small, even as small as being in the nanogram range, and subsequently directly processed by molecule analytic techniques.

BACKGROUND

Obtaining a sufficiently pure sample of biological molecules such as DNA, RNA, and proteins for purposes of experimentation can be a difficult task but is often a required step to performing a wide array of experiments.

The process generally begins with a scientist performing a synthesis step to generate the molecules desired. The molecules desired may be DNA, RNA, proteins, or other large molecules.

In some embodiments a plasmid containing genetic code to synthesize a specific protein may be inserted into microbial cells. The plasmid may also contain a specific antibiotic resistance, such that any microbial cells that did not receive the plasmid successfully may be eliminated by an antibiotic. A single colony of the microbial cells may then be selected, transferred to a growth medium, and grown until a desired cell density is obtained. Next, an activator molecule may be added to the growth medium to cause the microbial cells to produce the desired protein. The microbial cells, at that stage, will contain within them the specific protein in addition to all the other components of the cells. At that stage, various filtration and purification techniques may be used to isolate the specific protein. Alternatively, samples may be prepared from endogenous material, such as human tissue homogenates or human blood cell lysates.

One filtration and concentration technique, dead end filtration, allows a solution containing the specific protein to be concentrated while simultaneously removing other components of the solution that are smaller than a molecular weight cut off ("MWCO") of a membrane at the end of the dead end filtration device. While this may be an effective technique for concentrating and removing smaller contaminants, this technique may often cause the membrane to become clogged and slow down. Dead end filtration also often accepts only small amount of solution at a time, so the scientist may need to repeatedly refill the dead end filtration device with solution containing the specific protein.

Another filtration and concentration technique, cross flow filtration, allows for the scientist to feed a large amount of solution without needing to stop and refill periodically by continually causing the solution to flow across a membrane, such that solution and contaminants pass through the membrane, while the solution and large molecules do not pass through the membrane. After the solution passes over the membrane, it may be recycled for further purification. Over time, as solution and contaminants pass through the membrane, but the specific protein does not, the concentration of the specific protein increases.

Most existing techniques for purification of molecules are directed towards relatively large sample sizes. Scientists often face difficulty in effectively isolating and purifying molecules at relatively low sample sizes, such as at the nanogram scale. Scientists may need to operate with these extremely small sample sizes for many reasons. Some reasons may be that the sample utilizes a radioactive isotope, the sample may interact with itself, or the sample is difficult to produce at all.

Accordingly, what is needed is a system and apparatus that may more effectively filter, purify, and concentrate a desired biological molecule, especially at low concentrations.

SUMMARY

To minimize the limitations in the prior art, and to minimize other limitations that will become apparent upon reading and understanding the present specification, the present invention is directed to a frit used to support a membrane under high pressure.

One embodiment may be a frit comprising: a main body; and a plurality of grooves; wherein the main body may be configured to be received by a reservoir; wherein the reservoir may be a part of a molecular filtration device that may comprise an upper portion and a lower portion; wherein the upper portion may comprise two upper ports; wherein the two upper ports comprise a first upper port and a second upper port; wherein the first upper port may be configured to receive a first upper flow device; wherein the second upper port may be configured to receive a second upper flow device; wherein the lower portion may comprise a lower port and the reservoir; wherein the lower port may be configured to receive a lower flow device; wherein the upper portion may comprise a channel forming lip; wherein a channel forming cavity may be formed by the channel forming lip when the upper portion and the lower portion engage one another; wherein a lower sealing surface of the upper portion and an upper sealing surface of the lower portion are configured to receive a membrane; and wherein a channel may be defined by the channel forming cavity and the membrane. The plurality of grooves may be substantially parallel to one another and extend longitudinally across a surface of the main body. The plurality of grooves may comprise at least two different lengths. The frit may further comprise a drain hole. The frit may further comprise a transverse crossing lane; wherein the transverse crossing lane may be substantially perpendicular to the plurality of grooves. The drain hole may be located within the transverse crossing lane. The drain hole may be located at a center of the transverse crossing lane. The frit may further comprise a perimeter lip; wherein the perimeter lip extends around a shape of the main body. The reservoir may comprise a frit supporting lip; wherein the frit supporting lip may be configured to support the perimeter lip. The frit may comprise a porous structure. The frit may be rigid. The main body may be teardrop shaped, oval shaped, or elongated rectangle shaped.

The device of the present disclosure may be a frit configured to support a membrane used to filter and purify molecules having a size greater than a desired MWCO.

The device of the present disclosure may be removed from support of a membrane and re-used.

The device of the present disclosure may be a frit comprising substantially parallel grooves that reduce the amount of dead space impacting flow of solution, especially in small volume applications. This may be beneficial due to preventing undesirable build-up of certain molecules in specific locations due to directing flow.

The frit of the present disclosure may be used to purify molecules. The purified molecules may be eluted in sufficiently high concentrations for further purification without requiring additional concentration or processing.

The contents of this summary section are provided only as a simplified introduction to the disclosure and are not intended to be used to limit the scope of the claims. These, as well as other components, steps, features, objects, benefits, and advantages, will now become clear from a review of the following detailed description of illustrative embodiments, and of the claim.

BRIEF DESCRIPTION OF THE DRAWINGS

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

DETAILED DESCRIPTION OF THE ILLUSTRATIVE EMBODIMENTS

Figure 1:
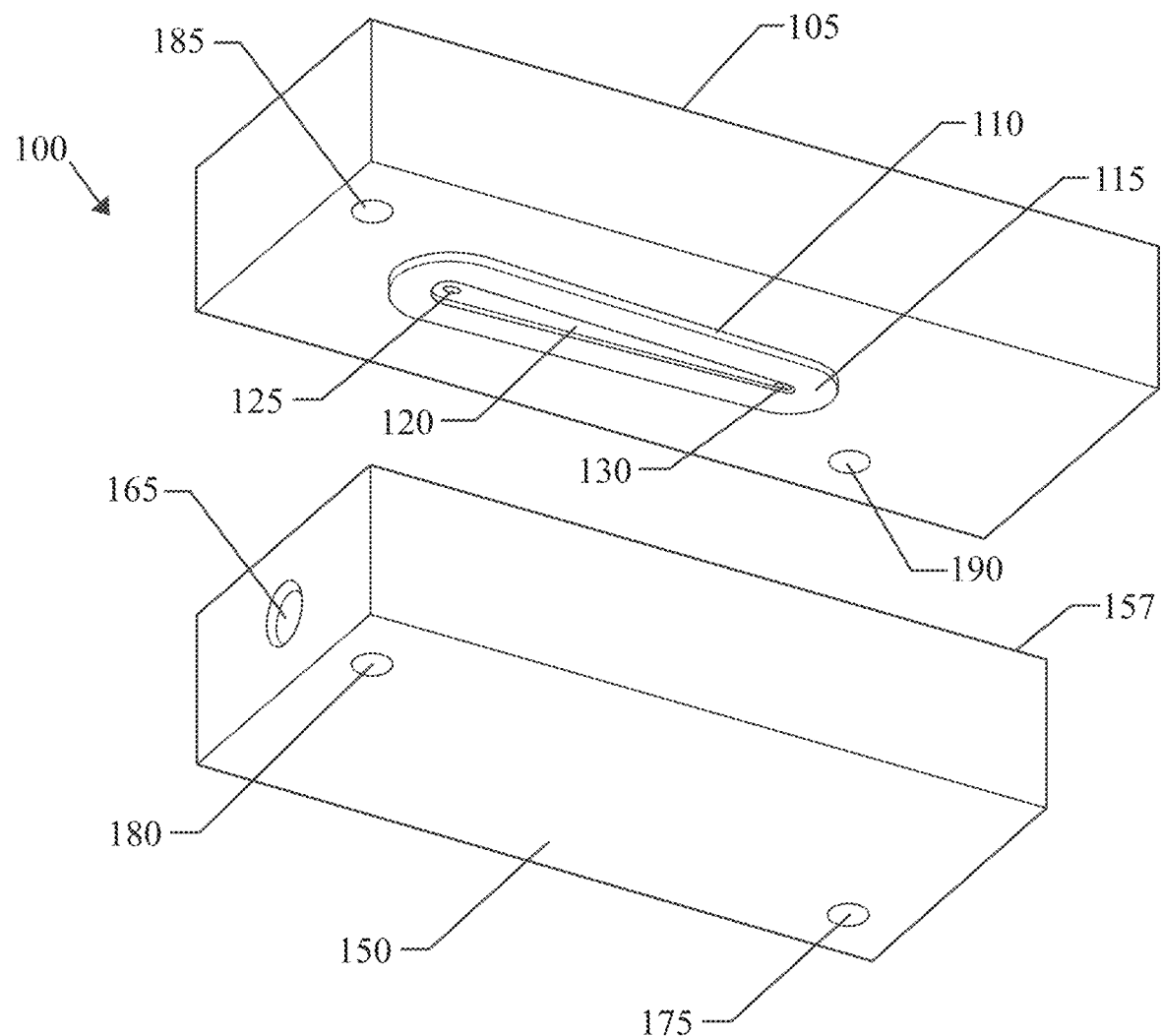
FIG. 1 is an illustration of a perspective view of one embodiment of a molecular filtration device.

Before the present device, methods, and systems are disclosed and described, it is to be understood that the methods and systems are not limited to specific device and methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that may be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all embodiments of this application including, but not limited to, steps in disclosed methods. Thus, if there are a variety of additional steps that may be performed it is understood that each of these additional steps may be performed with any specific embodiment or combination of embodiments of the disclosed methods.

The present methods and systems may be understood more readily by reference to the following detailed description of preferred embodiments and the examples included therein and to the Figures and their previous and following description.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 0.001-10% from the indicated number or range of numbers.

As used herein, "ul" refers to microliter, "ml" refers to milliliter, and "ng" refers to nanogram.

Various embodiments are now described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

Various embodiments presented in terms of systems may comprise a number of components, modules, and the like. It is to be understood and appreciated that the various systems may include additional components, modules, etc. and/or may not include all of the components, modules, etc. discussed in connection with the figures. A combination of these approaches may also be used.

Figure 3:
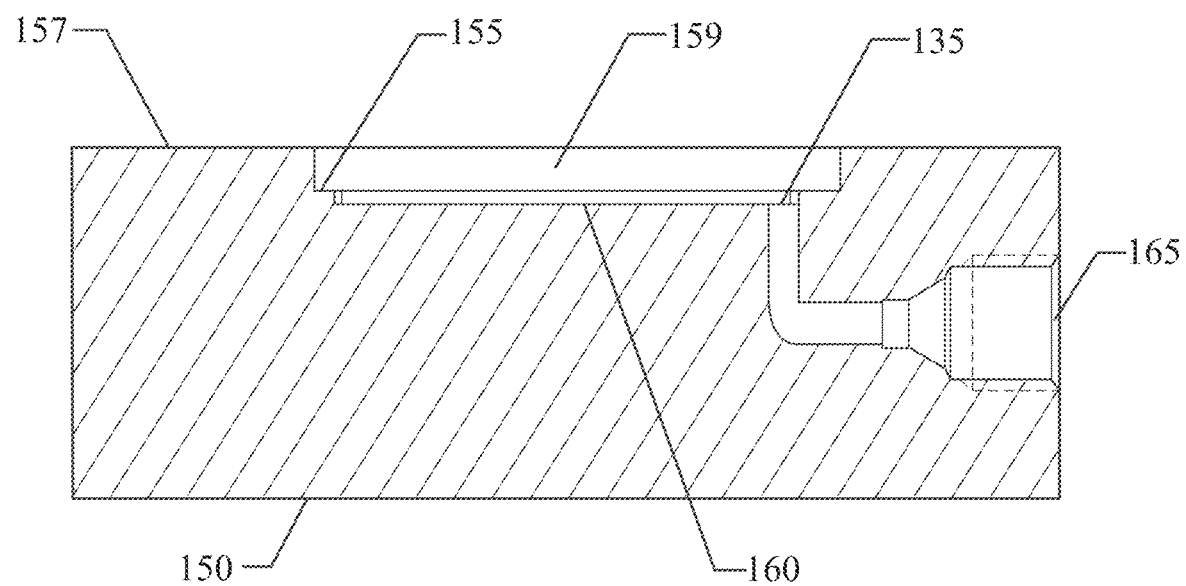
FIG. 3 is an illustration of a cross-sectional view of one embodiment of a lower portion of the molecular filtration device.
Figure 4:
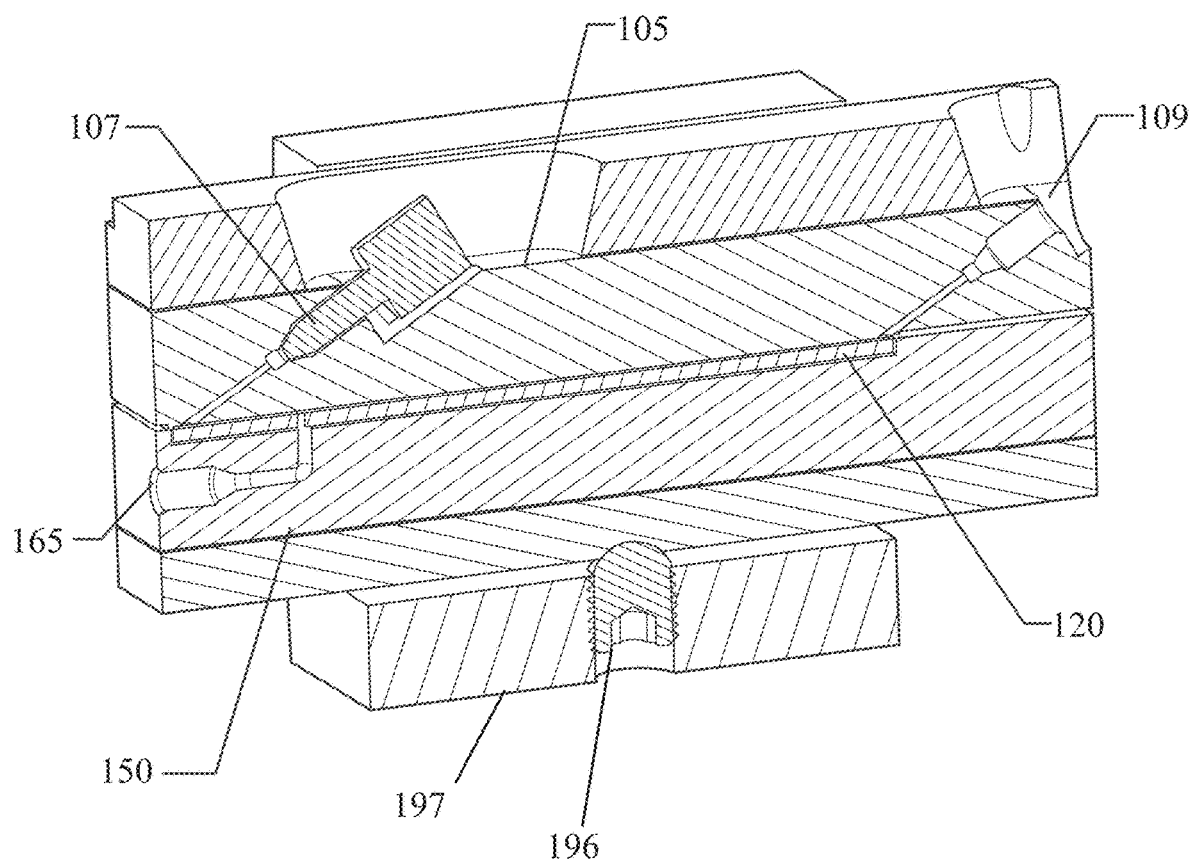
FIG. 4 is an illustration of a cross-sectional view of one embodiment of the upper portion and lower portion of the molecular filtration device in an assembled configuration.
Figure 5:
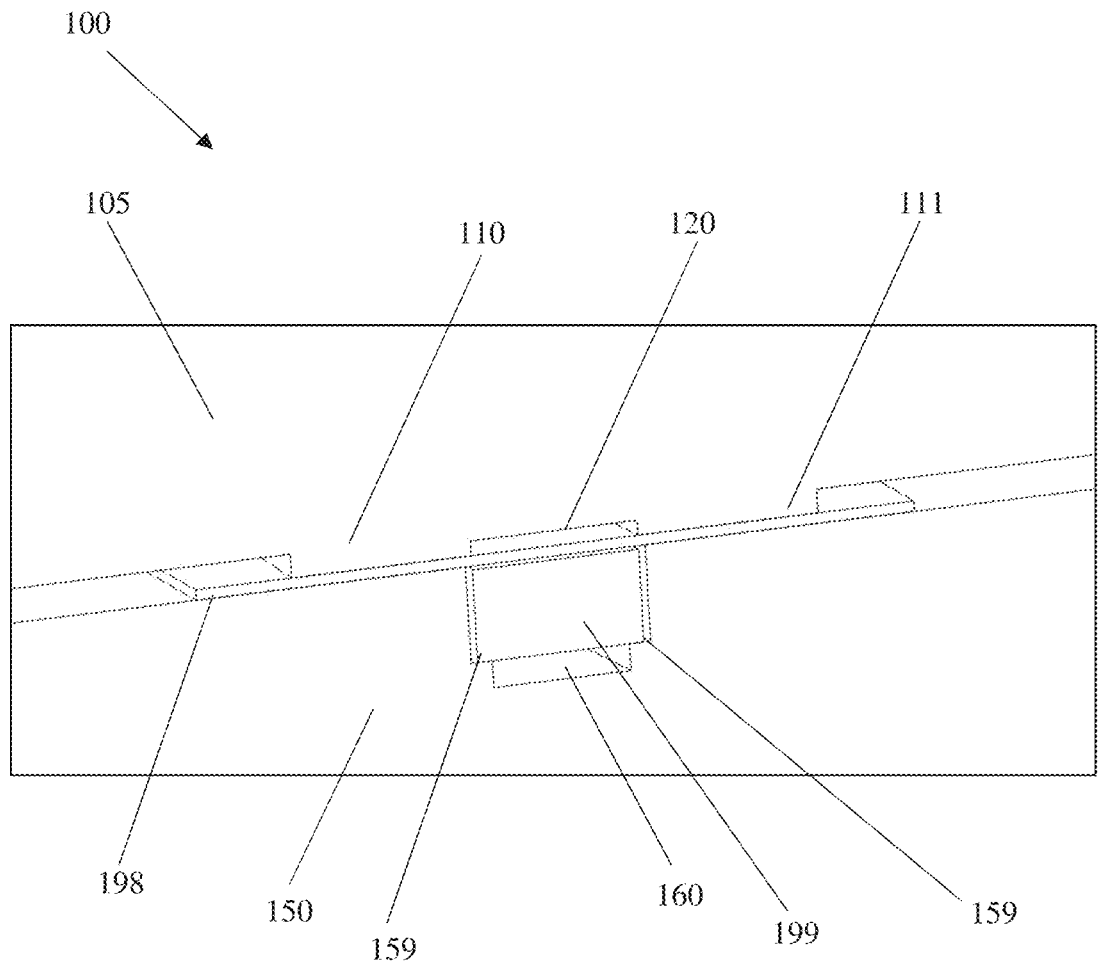
FIG. 5 is an illustration of a cross-sectional view of one embodiment of the molecular filtration device including a frit.

FIG. 1 is an illustration of one embodiment of a molecular filtration device. As shown in FIG. 1, the molecular filtration device 100 may comprise an upper portion 105 and a lower portion 150. The upper portion 105 may comprise a first upper port 125, second upper port 130, channel forming lip 110, and upper securing structures 185, 190. The lower portion 150 may comprise an upper sealing surface 157, a lower port 165, and lower securing structures 175, 180. As shown in FIGS. 3-5, detailed more fully herein below, the lower portion 150 may also comprise a frit portion 159, frit supporting lip 155 (as shown in FIG. 3), and reservoir 160.

The first upper port 125 and second upper port 130 may be configured to receive solution flow devices, wherein the solution flow devices may be connected to pumps through solution transfer structures such that each of the flow devices may be able to independently adjust the flow rate through the upper ports 125, 130, including reversing the flow direction of the solution. For example, the flow of solution may be such that the solution is ejected from the first upper port 125 and taken up by the second upper port 130. Alternatively, solution may be ejected from both the first and second upper ports 125, 130.

Similar to the first and second upper ports 125, 130, the lower port 165 may be configured to receive a lower flow device configured to inject or withdraw solution from the reservoir 160. As used herein, the terms inject and withdraw do not necessarily denote the mechanism for causing flow of solution, but rather are used to denote the direction of flow of solution.

The channel forming lip 110 may be a protrusion of the upper portion 105 comprising a lower sealing surface 115. The channel forming lip 110 may comprise a channel forming cavity 120, wherein when the lower sealing surface 115 of the upper portion 105 and the upper sealing surface 157 of the lower portion 150 are engaged with a membrane in between them, such that the channel forming cavity 120 forms a channel.

The first and second upper ports 125, 130 may allow for the flow of solution into and/or through the channel formed by channel forming cavity 120, depending on the direction of the flow of solution through the first and second upper ports 125, 130.

In a preferred configuration, a membrane may be placed and secured between the upper sealing surface 157 of the lower portion 150 and lower sealing surface 115 of the upper portion 105 when the upper sealing surface 157 and lower sealing surface 115 are fitted together and engaged. The membrane may allow for molecules of a certain size or characteristic to pass through, while preventing other, often larger, molecules from passing through the membrane. The membrane may be subjected to relatively high pressure due to the upper ports 125, 130 injecting liquid into the channel, with pressures reaching as high as 1,500 psig, or as low as 0 psig. Generally, the higher the pressure that is applied to the membrane, the faster the solution may pass through the membrane, provided the membrane is not structurally compromised by the higher pressure. One method of increasing the maximum operational pressure for the membrane is to provide the membrane with an additional rigid support structure, such as a frit.

In one embodiment, the first and second upper ports 125, 130 may be configured to inject a solution comprising desired molecules for isolation and purification, along with other, non-desired molecules, into the channel formed by the membrane and the channel forming cavity 120. As solution is injected into the channel formed by the membrane and the channel forming cavity 120, pressure increases, and the solution, along with molecules capable of passing through the membrane, may pass through the membrane, thereby passing into the reservoir 160 (shown in FIG. 3) and then out through the lower port 165. After a desired amount of the solution has passed through the membrane, the desired molecules may be concentrated in the channel formed by the membrane and the channel forming cavity 120, and on the membrane. In order to elute the desired molecules, the flow direction of the second upper port 130 and the lower port 165 may be reversed, such that the solution may be injected into the reservoir 160 and the channel formed by the membrane and the channel forming cavity 120 through the lower port 165 and first upper port 125, respectively, and the solution may be eluted from the second upper port 130. Alternatively, the first upper port 125 may allow for no flow, such that flow is solely from the lower port 165 to the second upper port 130. By this process, the solution having the desired molecule may be eluted through the second upper port 130 in a relatively small volume of solution or buffer.

In a preferred embodiment, very dilute amounts of molecules in relatively large volumes may be pushed through the first and second upper ports 125, 130 until substantially all of the desired molecules are in the channel formed by the membrane and the channel forming cavity 120. A buffer solution having a desired characteristic may then be run through the first and second upper ports 125, 130 in order to wash the desired molecule and ensure that all of the non-desired molecules capable of passing through the membrane are passed through the membrane, such as into a waste container. At that point the now concentrated and purified desired molecules may be retrieved through the second upper port 130. A buffer container may then be connected to the lower port 165 to inject a buffer into the reservoir 160, such that the desired molecule in the buffer solution is eluted into the second upper port 130 for collection and further use.

The upper portion 105 and lower portion 150 may be made of stainless steel, or other material of suitable strength and general non-reactivity. The membrane may be made of regenerated cellulose, polyether sulfone, cellulose acetate or other material that may create pore sizes of defined size and distribution.

Figure 2:
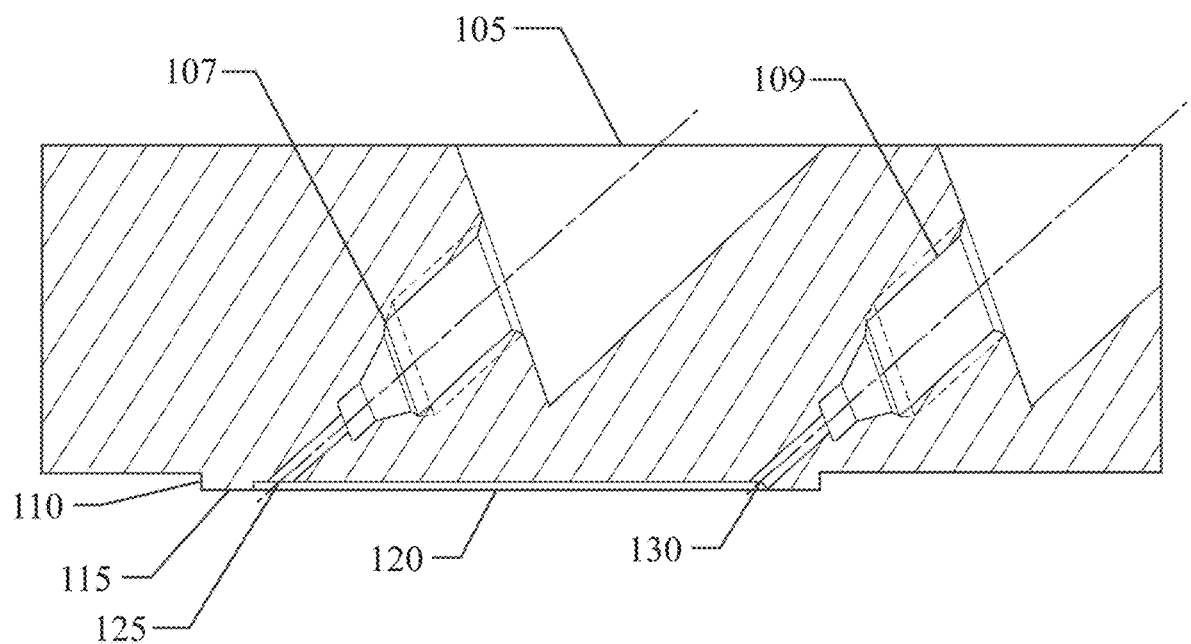
FIG. 2 is an illustration of a cross-sectional view of one embodiment of an upper portion of the molecular filtration device.

FIG. 2 is an illustration of a cross-sectional view of one embodiment of an upper portion of the molecular filtration device. As shown in FIG. 2, the first upper flow device 107 and second upper flow device 109 may be configured to engage the first upper port 125 and second upper port 130, respectively. The channel forming cavity 120 may be extremely small in volume relative to the upper portion 105. The channel forming cavity 120 may be about 5 uL to about 50 uL. In one embodiment, the channel forming cavity 120 may be about 14.6 uL.

FIG. 3 is an illustration of a cross-sectional view of one embodiment of a lower portion of the molecular filtration device. As shown in FIG. 3, the lower portion 150 may comprise an upper sealing surface 157, top end of lower port 135, frit receiving portion 159, frit supporting lip 155, and reservoir 160. The lower end of lower port 165 may be configured to receive a lower flow device.

FIG. 4 is an illustration of a cross-sectional view of one embodiment of the upper portion and lower portion of the molecular filtration device in an assembled configuration. As shown in FIG. 4, the first upper flow device 107 and second upper flow device 109 may be angled relative to the channel forming cavity 120. In one embodiment, the upper flow devices 107, 109 may be between 15 and 165 degrees relative to the bottom surface of the upper portion 105.

The molecular filtration device 100 may also comprise a pressure application mechanism 197, which may be configured to apply a force such that the upper portion 105 and lower portion 150 are pressed toward one another. This pressure application mechanism 197 may be used to apply a specific pressure to a membrane placed between the upper portion 105 and lower portion 150. Pressure may be adjusted by turning the set screw 196.

FIG. 5 is an illustration of a cross-sectional view of one embodiment of the molecular filtration device including a frit. As shown in FIG. 5, when the upper portion 105 and lower portion 150 are fitted together and engaged, a membrane 198 and frit 199 may be compressed between the upper portion 105 and lower portion 150. In one embodiment, the molecular filtration device 100 may be assembled as by placing the frit 199 on the frit supporting lip 159 of the lower portion 150. On top of the frit 199, the membrane 198 of a desired permeability may be placed. Then, on top of the membrane 198, the upper portion 105 may be placed, such that the channel forming lip 110, 111 engages the membrane 198. The frit 199 preferably may have a permeability higher than that of the membrane 198. As shown in FIG. 5, the channel 120 may be a cavity enclosed by the upper portion 105, channel forming lip 110, 111, and membrane 198, wherein the membrane 198 may be structurally supported by the frit 199.

Figure 6:
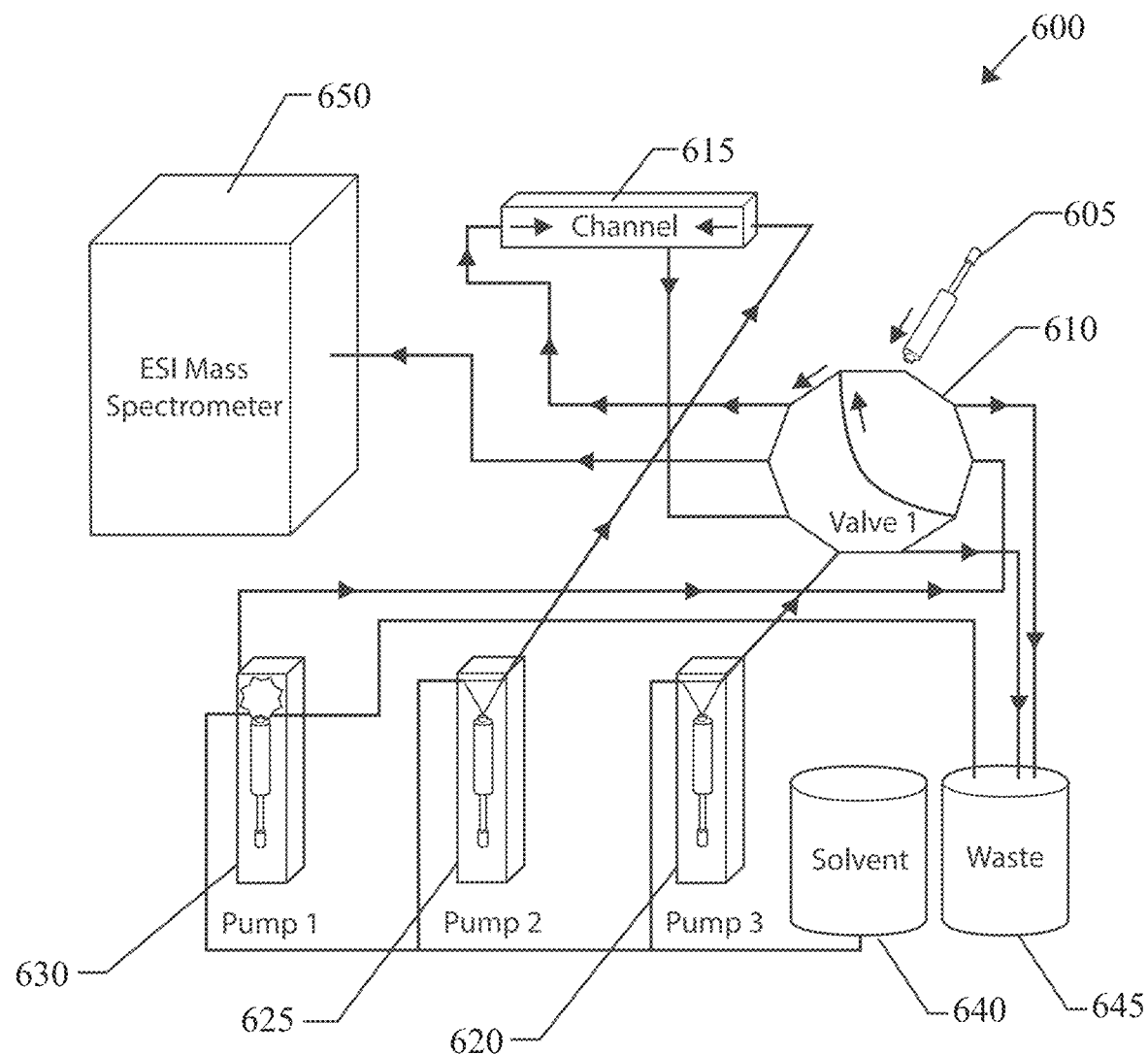
FIG. 6 is a diagram showing the molecular filtration device being prepared for use.

FIG. 6 is a diagram showing the molecular filtration device being prepared for use. As shown in FIG. 6, one embodiment of the molecular filtration system 600 may comprise an injection mechanism 605, injection valve 610, molecular filtration device 615, first pump 630, second pump 625, third pump 620, solvent container 640, waste container 645, and analysis machine 650.

In one embodiment the injection mechanism 605 may be a syringe and during a cleaning protocol, may be used to run a clean buffer solution through the injection valve 610. The pumps 620, 625, 630 may be configured to clean the entire system by flushing clean buffer solution through the flow lines, molecular filtration device 615, and into the waste container 645. After clean buffer is flushed through the flow lines, the sample may be introduced to the system. Specifically, a sample comprising a molecule for filtration and purification may be loaded into the injection mechanism 605 and injected into the injection valve 610. The first pump 630 may then pump the sample into the molecular filtration device 615 via a first upper port. At approximately the same time, the second pump 625 may pump a buffer solution from the solvent container 640 into the molecular filtration device 615 via a second upper port, and the resulting waste solution may be pumped into the analysis machine 650. Once the sample is completely loaded and washed such that impurities able to pass through a membrane of the molecular filtration device 615 are substantially or entirely removed, then what may remain in the molecular filtration device 615, specifically in the channel, may be a sufficiently pure sample.

Figure 7:
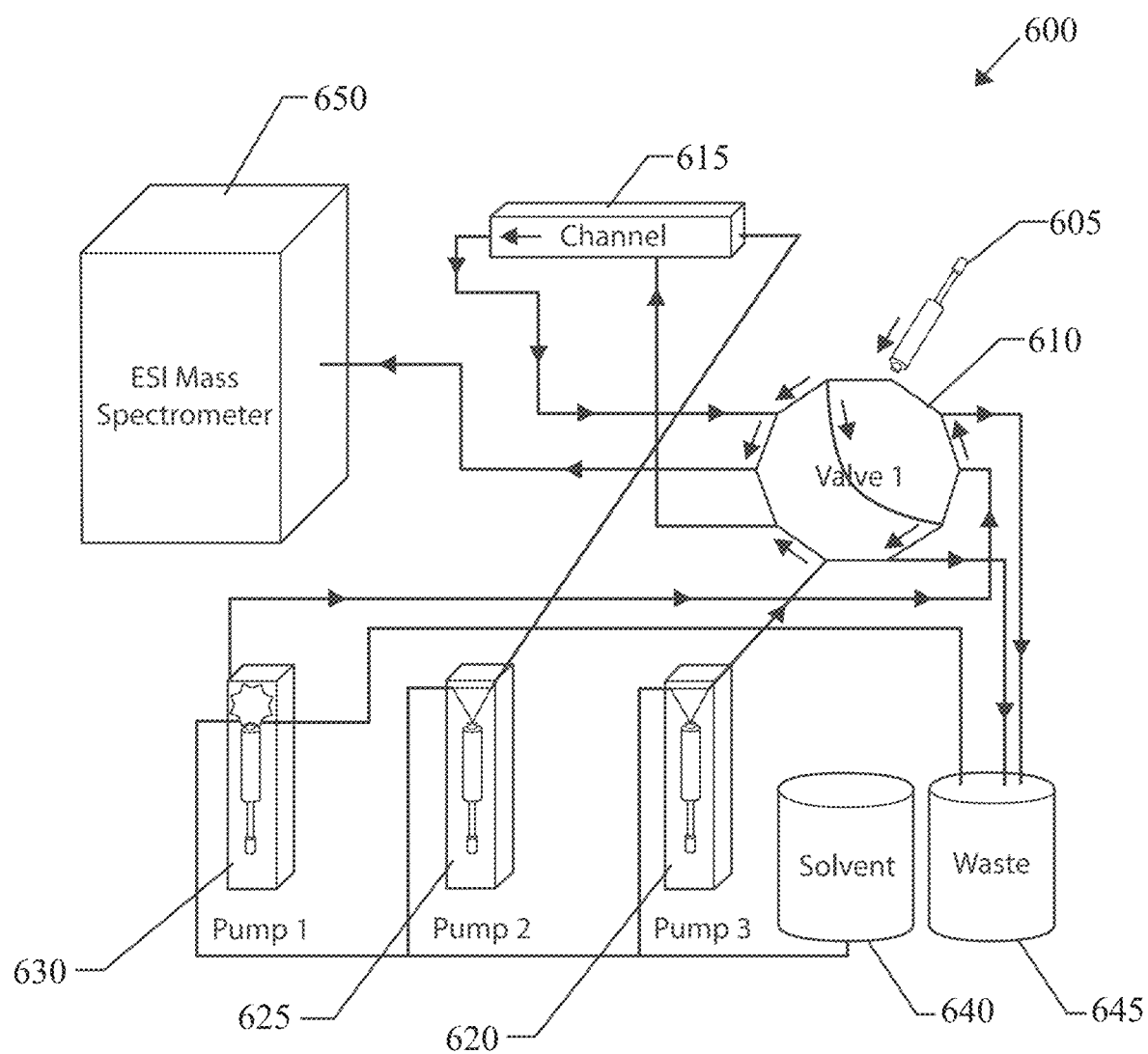
FIG. 7 is a diagram showing the molecular filtration device in use for elution and analysis.

FIG. 7 is a diagram showing the molecular filtration device in use for elution and analysis. After the molecular filtration device 615 contains a sufficiently pure sample, the direction of flow of the pumps 620, 625, 630 may be modified in order to efficiently elute the sample in a high concentration in order to allow for further analysis. Specifically, the second pump 625 may stop pumping, thereby effectively blocking the second port of the molecular filtration device 615. Solution may then be pumped into the lower port of the molecular filtration device 615, and then out of the first upper port and into the injection valve 610. The injection valve 610 may then be configured to directly pump the now purified sample into an analysis machine 650 for further analysis. The entire process shown in FIGS. 6 and 7 may be automated for ease of use and consistency. The analysis machine 650 may be any machine into which a sufficiently pure sample may be analyzed, such as a Mass Spectrometer.

In one embodiment more than one molecular filtration device 615 may be used in parallel. When more than one molecular filtration device 615 is used, the sample may be loaded in approximately 21 seconds, focused/washed in approximately 38 seconds, and eluted in approximately 33 seconds. Additionally, a sample may be loaded/focused on a first molecular filtration device while a sample in a second molecular filtration device is being eluted. In alternate embodiments, the molecular filtration device may proceed with being loaded while a sample is being eluted, in order to increase the throughput of sample in the molecular filtration device. In yet further embodiments, additional molecular filtration devices 615 may be used, provided that hardware is adequate to support said additional molecular filtration devices 615.

Figure 8A:
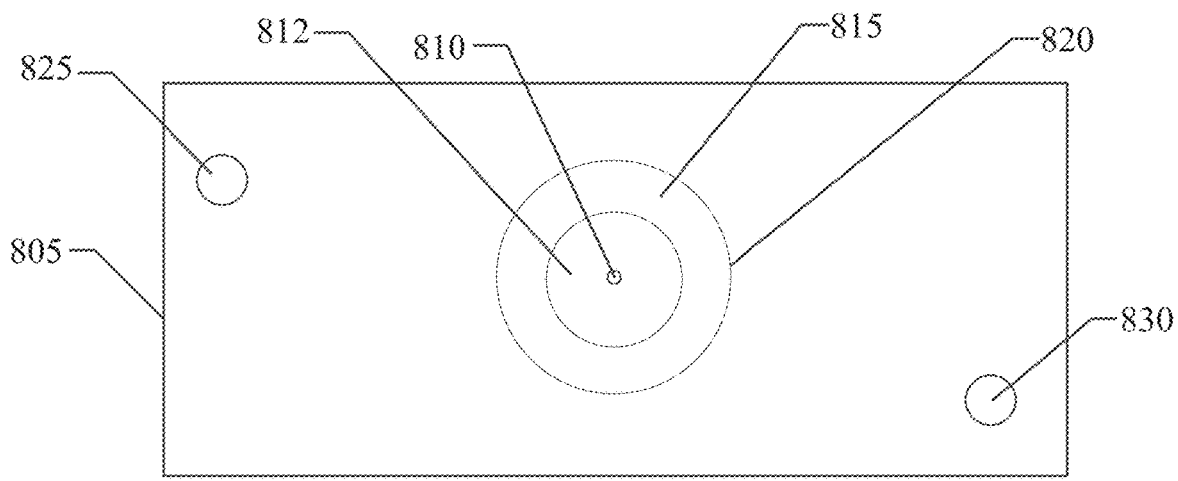
FIGS. 8A-C are illustrations of different channel shapes of the molecular filtration device.
Figure 8B:
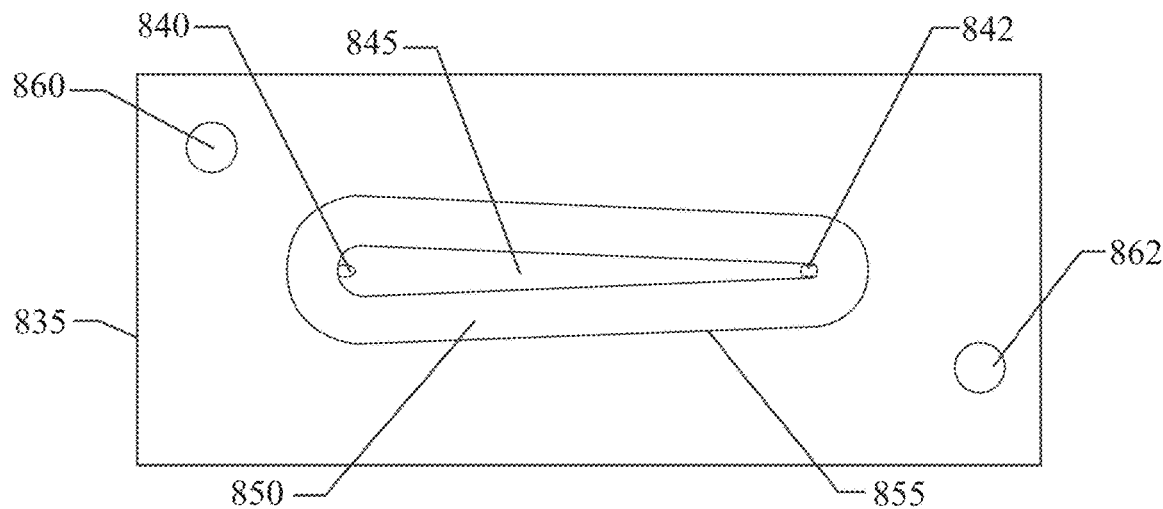
Figure 8C:
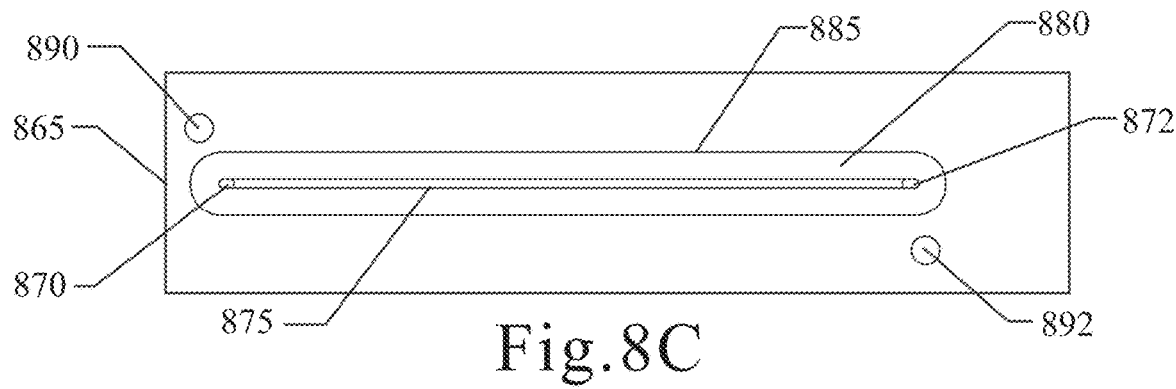

FIGS. 8A-C are illustrations of different channel shapes of the molecular filtration device.

As shown in FIG. 8A, an upper portion 805 may comprise a channel forming cavity 812 that is substantially circular in shape. In this embodiment, the upper portion 805 may have a single upper port 810. The shape of the channel forming cavity 812 may be substantially defined by the channel forming lip 820 and its lower sealing surface 815. The upper portion 805 may also comprise securing structures 825, 830.

As shown in FIG. 8B, an upper portion 835 may comprise a channel forming cavity 845 that is substantially elongated teardrop in shape. In this embodiment, the upper portion 835 may have two upper ports 840, 842. The shape of the channel forming cavity 845 may be substantially defined by the channel forming lip 855 and its lower sealing surface 850. The upper portion 835 may also comprise securing structures 860, 862.

As shown in FIG. 8C, an upper portion 865 may comprise a channel forming cavity 875 that may be a substantially elongated oval shape. In this embodiment, the upper portion 865 may have a two upper ports port 870, 872. The shape of the channel forming cavity 875 may be substantially defined by the channel forming lip 885 and its lower sealing surface 880. The upper portion 865 may also comprise securing structures 890, 892.

Figure 9:
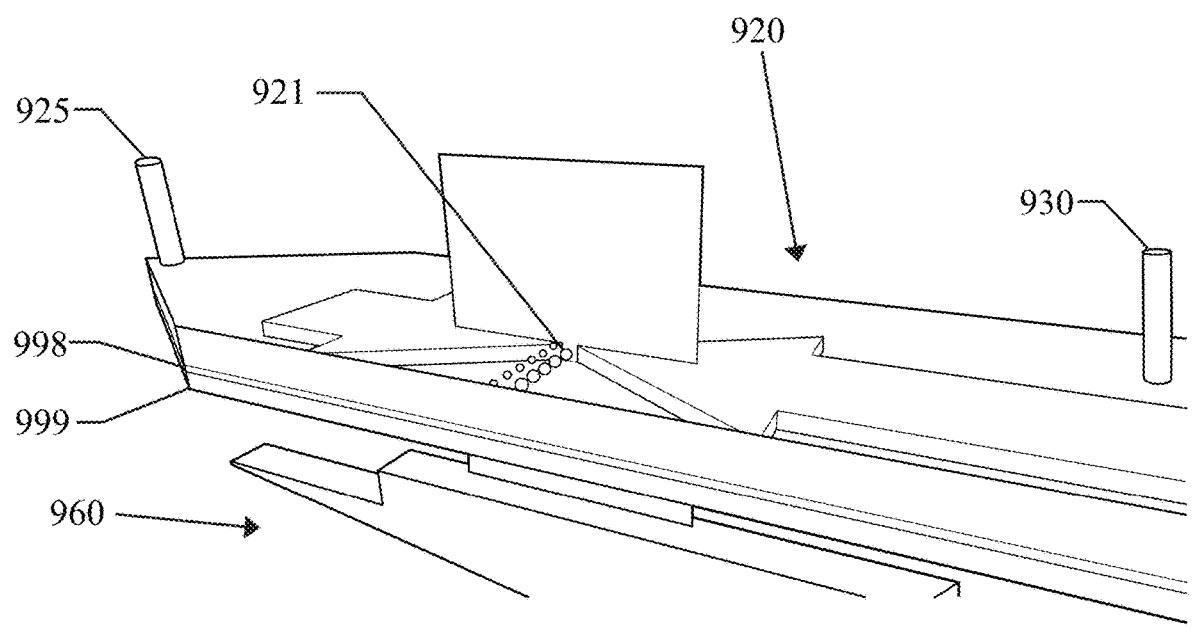
FIG. 9 is an illustration showing a channel of the molecular filtration device.

FIG. 9 is an illustration showing a channel of the molecular filtration device. As shown in FIG. 9, the channel 920 may have solution pumped into it via a first upper port 925 and second upper port 930, which may cause molecules to create a band 921 near a substantial midpoint of the flow caused by the first upper port 925 and second upper port 930. The flow of solution may then cause molecules, including solvent, smaller than a particular size to cross a membrane 998 and frit 999 and pass into the reservoir 960 or outflow mechanism. The creation of the band 921 allows for the membrane 998 to remain relatively unclogged, and allow for greater filtration, washing, and concentration of molecules caught in the band 921.

Experiment 1: Pressure Test on Compressed Membrane

Figure 10:
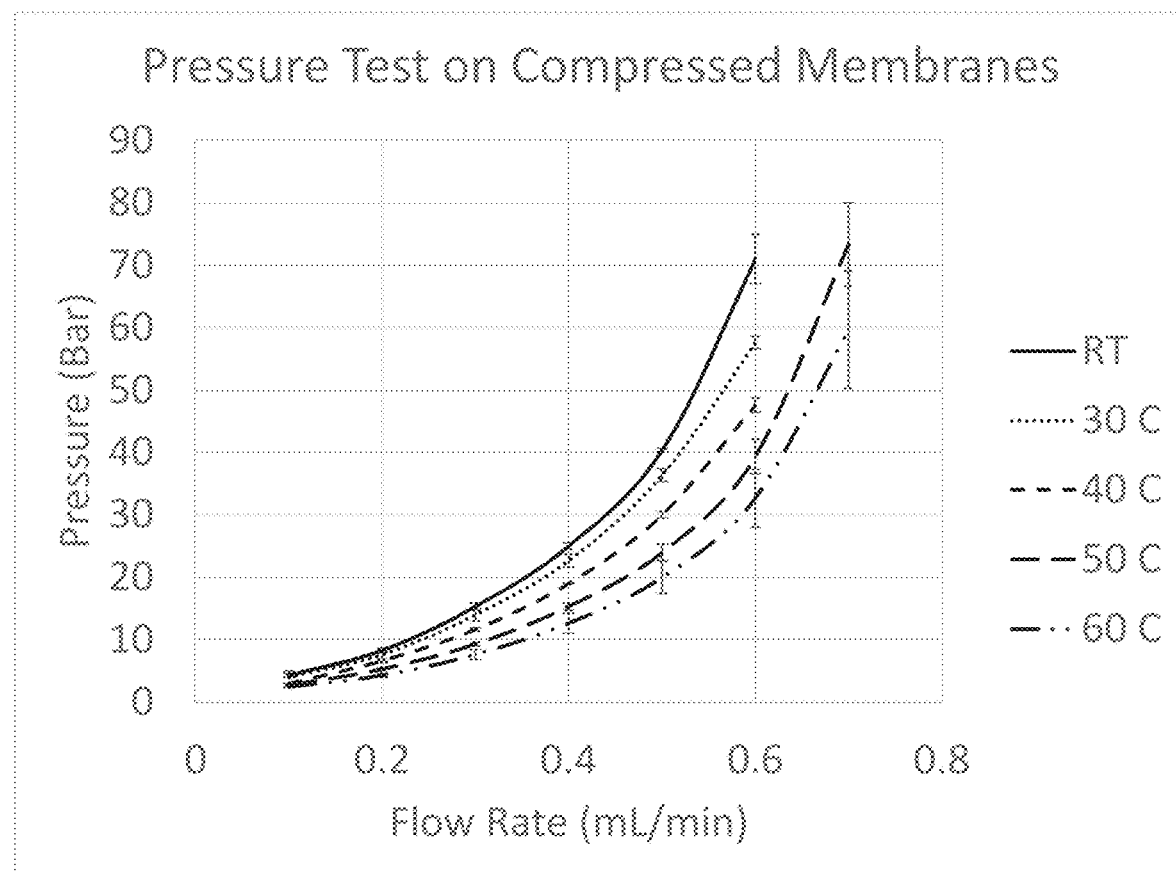
FIG. 10 is a graph showing flow rate v. pressure for compressed membranes in the molecular filtration device.

The effects of pressure on a membrane compressed by the device of the present disclosure was tested. A 10 kDa membrane was installed in a molecular filtration device, and the flow rate was increased until the pressure on the membrane by the flow of solution reached 100 bar. The results of this experiment are shown in FIG. 10. Importantly, it was discovered that the membrane being compressed by the molecular filtration device of the present disclosure must be pressurized up to 100 bar in order to allow for the pressure measurements to increase as observed by increasing flow rate. One potential explanation for this is that the spun support on which the membrane is cast may have been crushed, leading to increased back pressure.

Experiment 2: Behavior of Unpressurized Membrane

Figure 11:
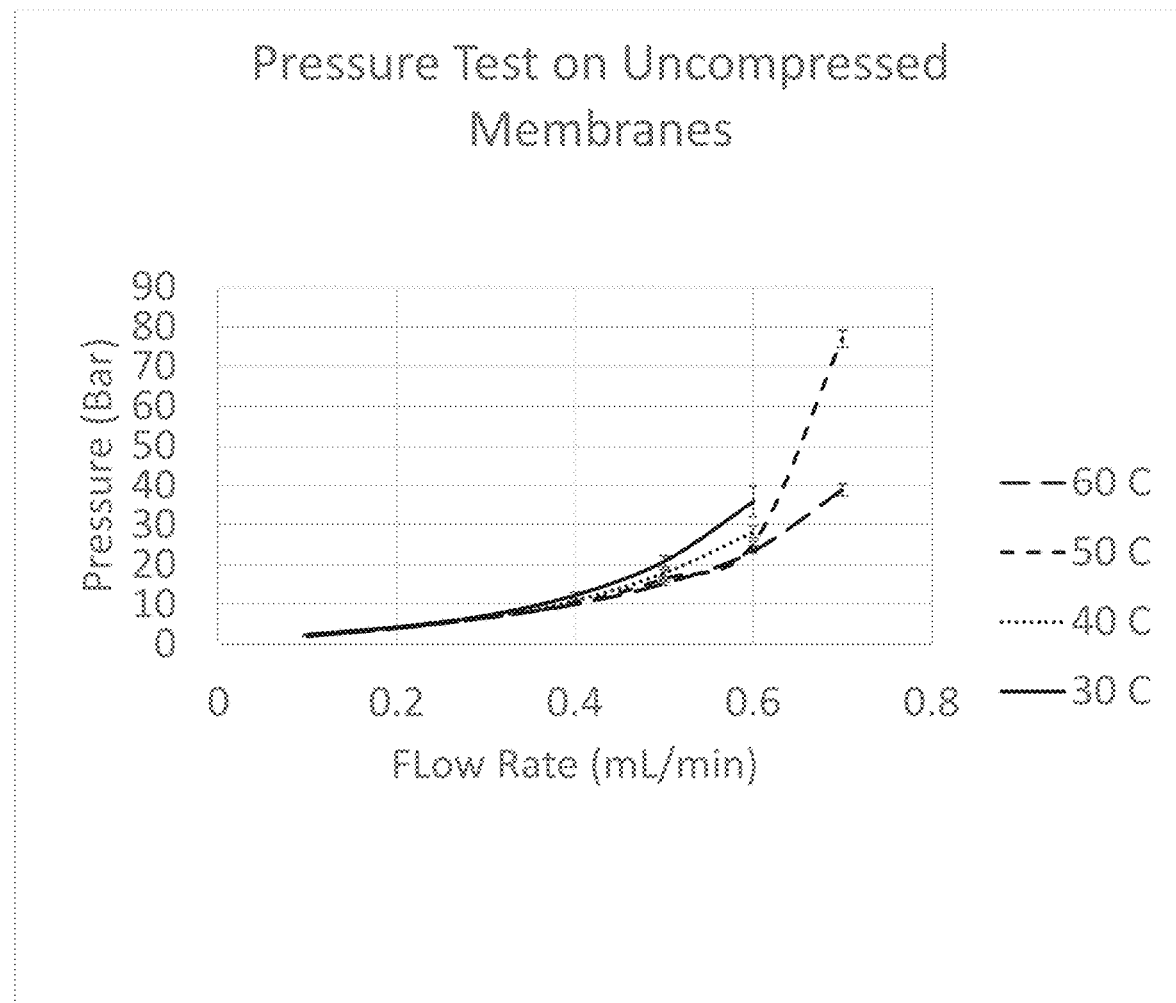
FIG. 11 is a graph showing flow rate v. pressure for uncompressed membranes in the molecular filtration device.

The effects of pressure on an uncompressed membrane was tested. A 10 kDa membrane was installed in a molecular filtration device, and flow rate was increased. The results of this experiment are shown in FIG. 11. Importantly, it was discovered that the pressure experienced by the uncompressed membrane, compared to the compressed membrane of Experiment 1 hereinabove, was significantly less than when the membrane was compressed. Additionally, when the membrane was uncompressed, the temperature of the experiment had a significantly smaller effect on the relationship between flow rate and pressure. The data shows that a useful forward flow rate may be around 500 uL/min.

Experiment 3: Reverse Flow Through Membrane

Figure 12:
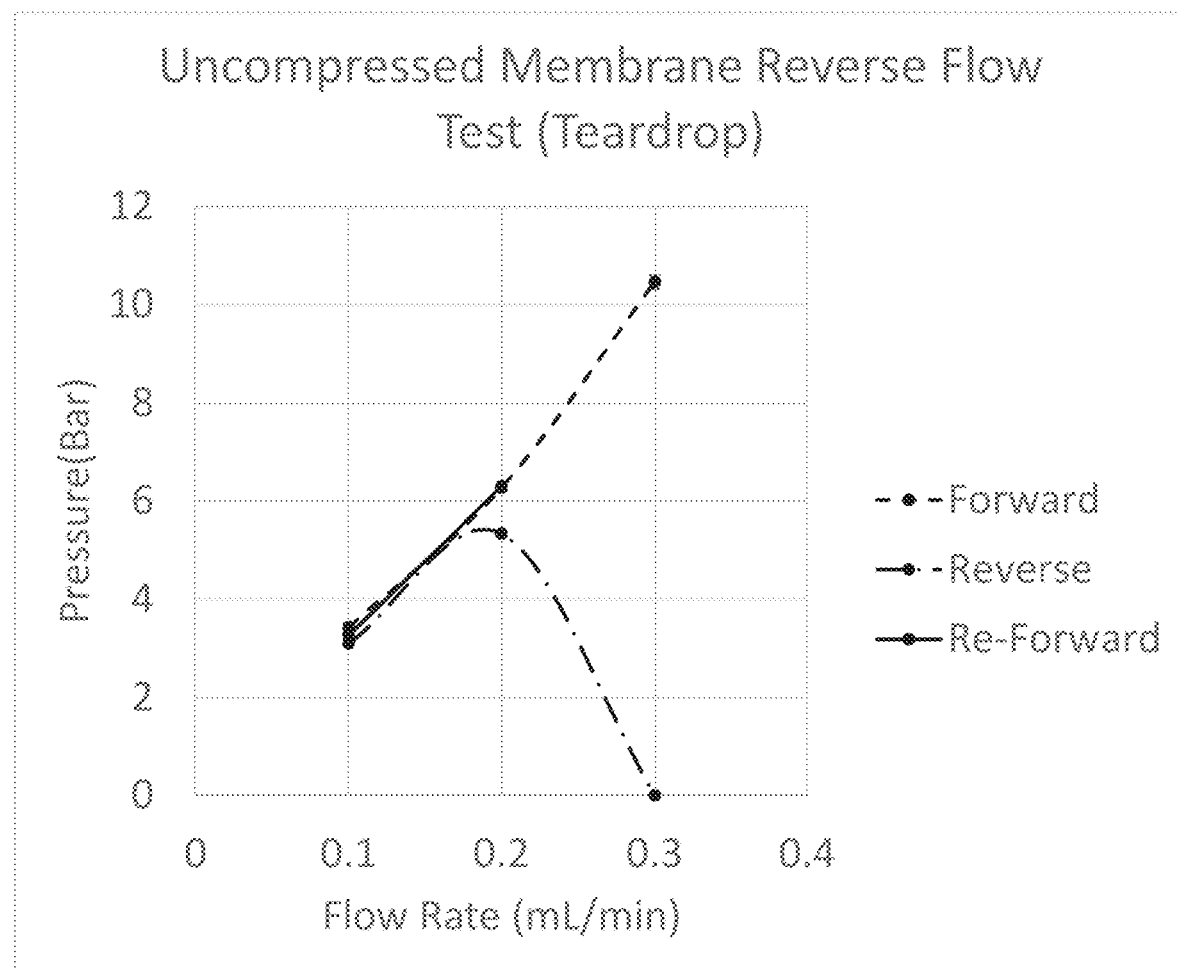
FIG. 12 is a graph showing flow rate v. pressure for different flow directions in the molecular filtration device.

The effects of reversing flow of solution at different flow rates was measured. A 10 kDa membrane was installed in a molecular filtration device, and the flow was forward, reversed, and then re-forwarded at increasing flow rates. The results of this experiment are shown in FIG. 12. The membrane experienced failure when in a reverse flow rate of between 200 and 300 uL/min were applied. Thus, a useful reverse flow rate was between 100 and 200 uL/min, which may be somewhat comparable to current 2.1 mm column chromatographic methods.

Experiment 4: Forward Flow Through Uncompressed 1 kDa Membrane

Figure 13:
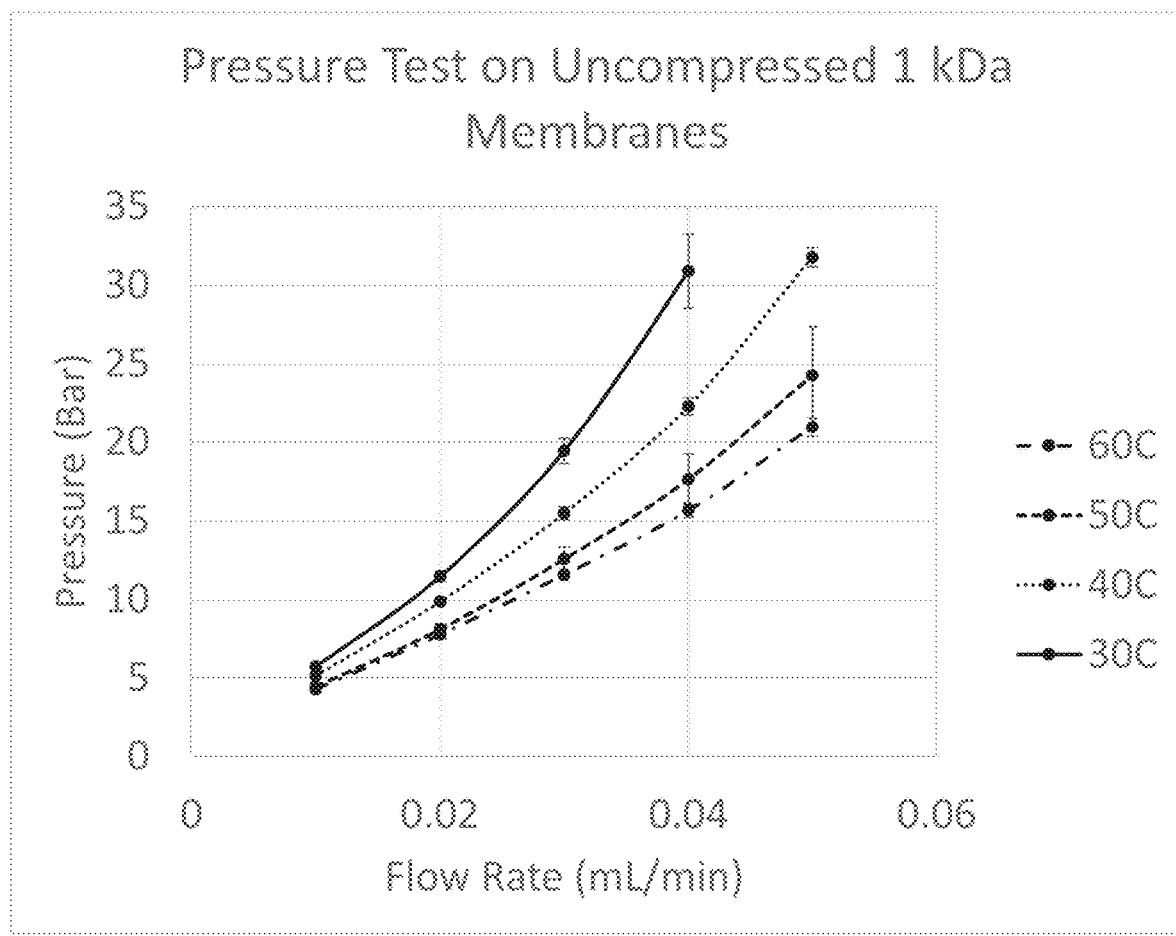
FIG. 13 is a graph showing flow rate v. pressure for uncompressed 1 kDa membranes in the molecular filtration device.

The effects of pressure on an uncompressed membrane was tested. A 1 kDa membrane was installed in a molecular filtration device, and flow rate was increased. The results of this experiment are shown in FIG. 13. The 1 kDa membrane experienced pressures approximately 10× that experienced by a 10 kDa membrane at similar flow rates. Experiments with 1 kDa membranes and 10 kDa membranes experienced similar pressures when the flow rate of the 10 kDa membrane was 10 times that of the 1 kDa membrane.

Experiment 5: Reverse Flow Through 1 kDa Membrane

Figure 14:
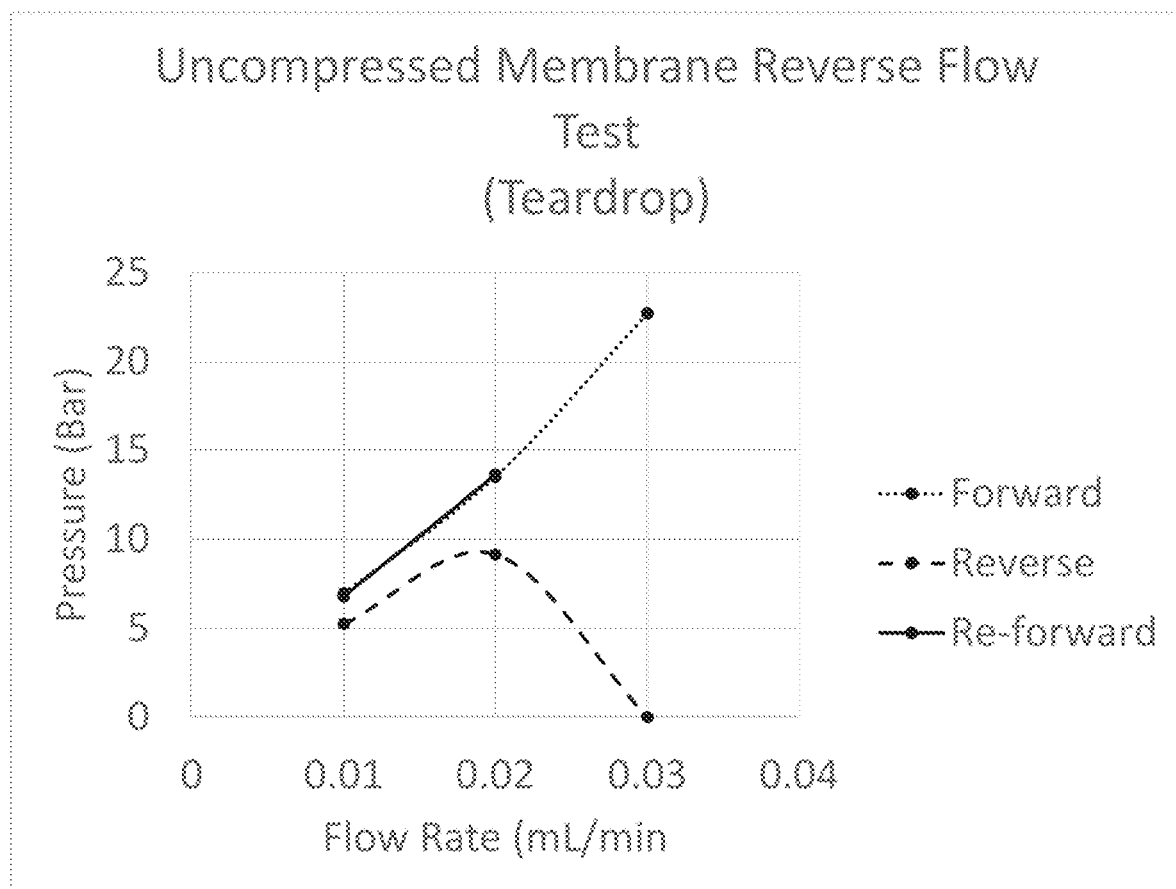
FIG. 14 is a graph showing flow rate v. pressure for different flow directions in the molecular filtration device with a 1 kDa membrane.

The effects of reversing flow of solution at different flow rates was measured. A 1 kDa membrane was installed in a molecular filtration device, and the flow was forward, reversed, and then re-forwarded at increasing flow rates. The results of this experiment are shown in FIG. 14. The membrane experienced failure when in a reverse flow rate of between 20 and 30 uL/min were applied. Thus, a useful flow rate, forward and backward, was between 10 and 20 uL/min. Similar to Experiment 3, the data indicates that the membrane becomes ruptured around 10 bar.

Experiment 6: Reverse Flow Analysis of Various Channel Geometries

Figure 15:
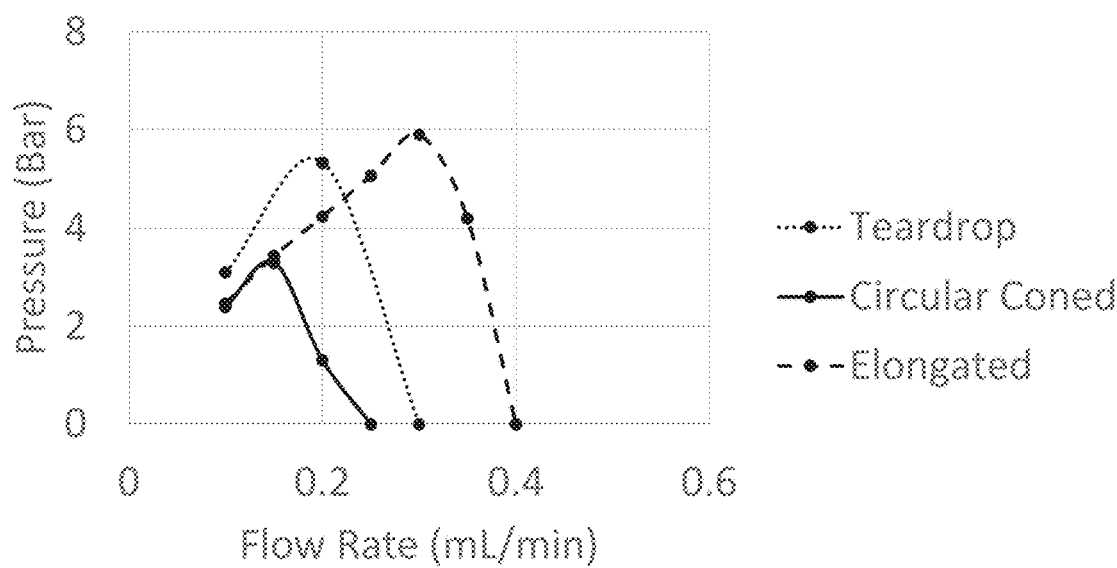
FIG. 15 is a graph showing the effects of channel geometry on membrane stability.

The effects of channel shape and its effects on membrane stability at different flow rates was measured. The results of this experiment are shown in FIG. 15. As shown in FIG. 15, the shape of the channel has a significant effect on the amount of pressure the membrane may be able to tolerate when flow is reversed before experiencing structural failure. Particularly, the elongated shaped channel is the most resilient, while the circular coned shaped channel is the least resilient of the three channel shapes tested. The teardrop shaped channel's resilience is between that of the elongated shape and circular cone shaped channels. The elongated channel has a 0.03 mm maximum span, and a 150 um channel height. The teardrop channel has a 0.125 mm maximum span and a 250 um channel height. The circular channel has a 0.343 mm maximum span, and a coned height of 250 um to 450 um or flat 150 um channel height.

An increased span generally results in a lower reverse membrane flow rate due to membrane lift resulting from no frit or supporting structure above the membrane.

Experiment 7: Comparison of Molecular Filtration Device and Standard Chromatography A comparison of the molecular filtration device and standard chromatography was conducted. Both the molecular filtration device and chromatography were analyzed by a Q Exactive™ Plus mass spectrometer, manufactured by Thermo Scientific™.

The chromatography included: 2.1 mm i.d. Agilent PLRP-S column; at 65 C; sample injection volume of 5 μL having 100 ng of sample; flow rate of 100 μL/min; A: 0.1% FA B: ACN+0.1% FA; and Gradient: 0 min 20% b; 2 min 20%; 4.75 min 65%; 5 min 80% b; 5.5 min 15%; 5.75 85%; 6 min 15%; 6.25 85%; 6.5 min 15% 1605.

The molecular filtration device had a flow rate of 100 uL/min, with a 100 uL sample injection volume having 100 ng of sample 1600.

Figure 16:
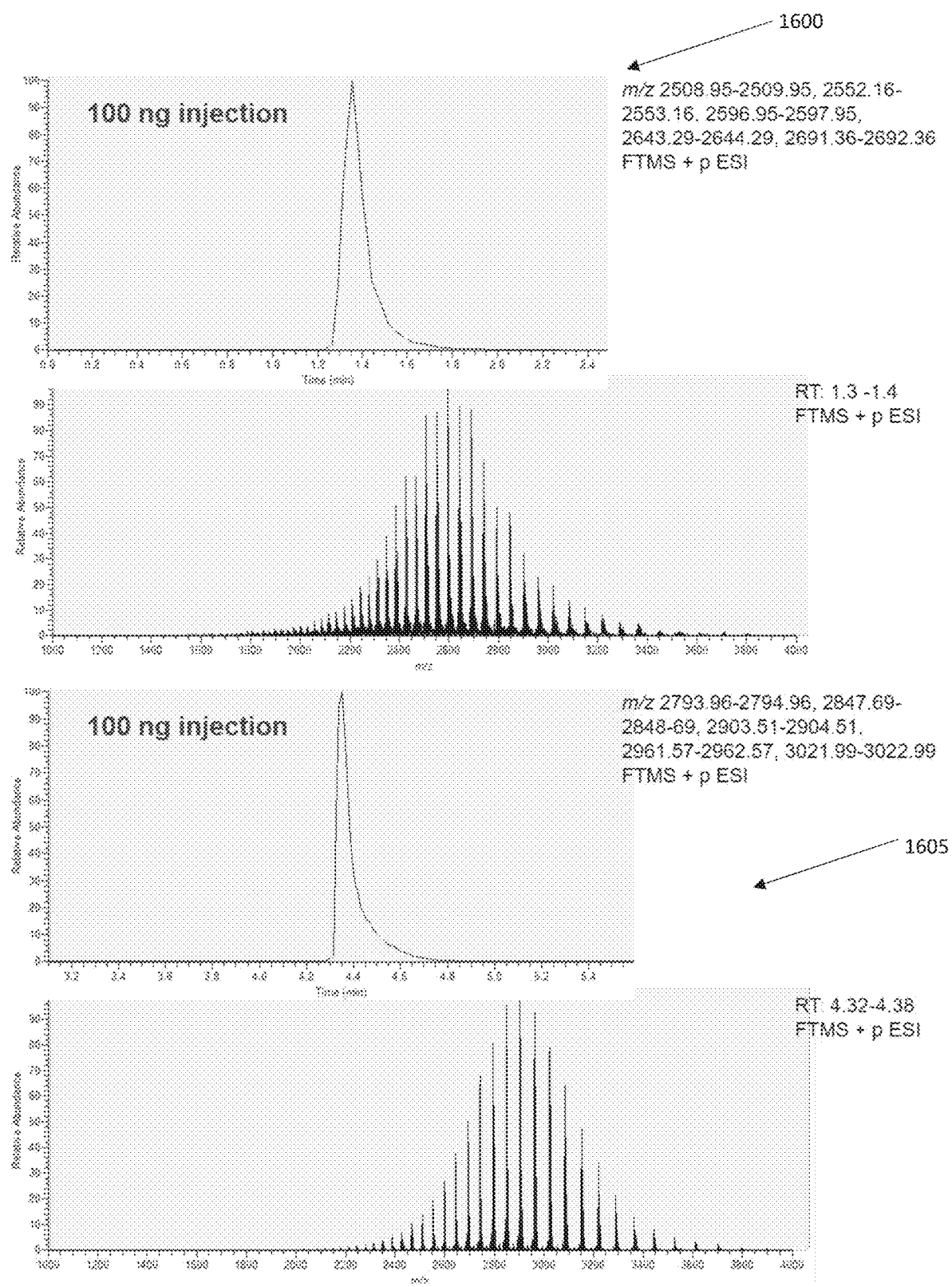
FIG. 16 is a set of graphs showing the efficacy of the molecular filtration device compared to traditional filtration methods.

As shown in FIG. 16, despite the fact that the chromatography method included a much smaller sample injection volume, the molecular filtration volume eluted the desired sample with in a band similar to that of chromatography. Further, the molecular filtration device was able to elute the sample much more quickly than the chromatography method. Accordingly, the molecular filtration device is highly effective at analyzing significantly more dilute samples than traditional methods, including liquid chromatography.

Experiment 8: Molecular Filtration Device to Mass Spectrometer

Figure 17:
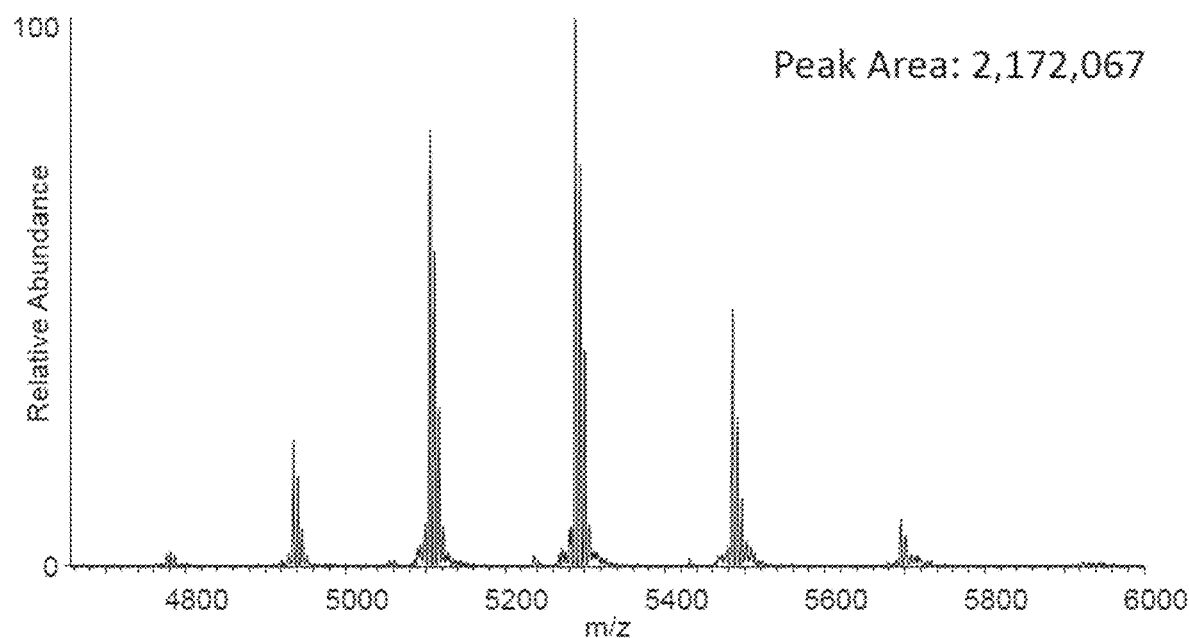
FIG. 17 is a graph showing data related to a sample processed by the molecular filtration device and transferred directly to a mass spectrometer, wherein the sample is 500 ng.
Figure 18:
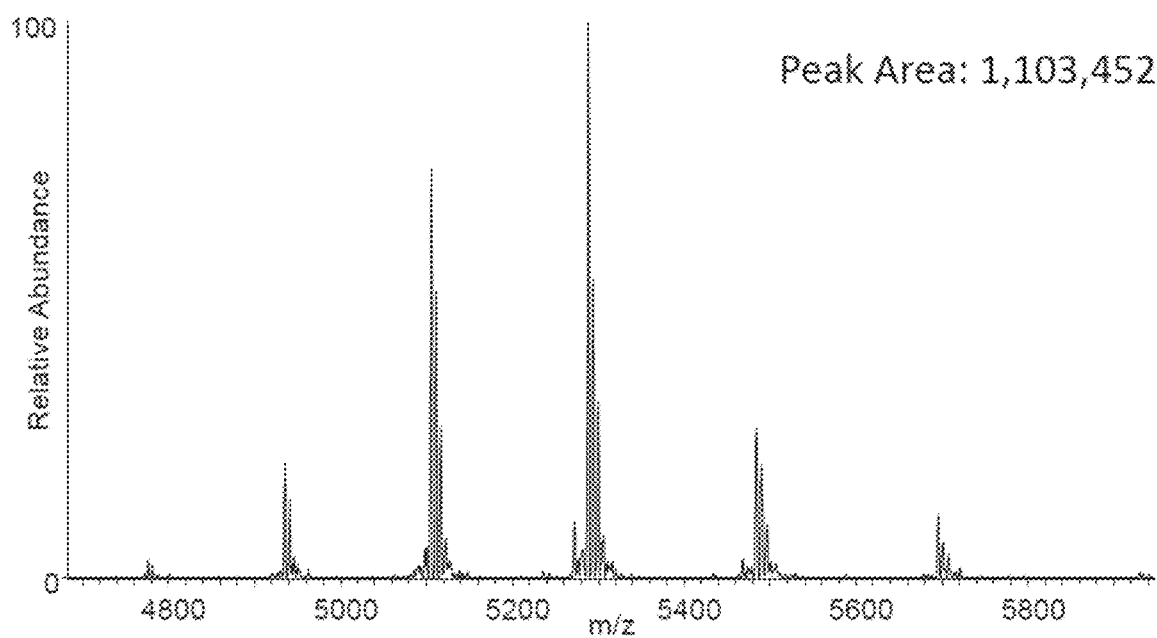
FIG. 18 is a graph showing data related to a sample processed by the molecular filtration device and transferred directly to a mass spectrometer, wherein the sample is 250 ng.

A sample of Herceptin in excipient was loaded onto a molecular filtration device and analyzed by a Q Exactive™ Plus mass spectrometer. A volume of 5 uL containing 250 ng or 500 ng of sample was loaded onto the molecular filtration device, was washed for 30 seconds with 300 uL, and eluted with 55 uL at a rate of 100 uL/min. The sample was eluted directly onto a mass spectrometer with 30 a.u. sheath; 10 a.u. aux; 300 C HESI probe; 275 C ion transfer tube; 100 V SID; 10 V HCD; Pressure reg setting: 4; 5 uscans; and 17,500 res @ m/z 200. The result of loading 500 ng is shown in FIG. 17 and the result of loading 250 ng is shown in FIG. 18.

The ratio of the peaks loaded is 0.508, which indicates a quantitative response and provided superior data to traditional methods of analysis. Further, the nature of the loading and washing of sample on the molecular filtration device allows for the ability for the user to change between denatured and native forms from run to run by specifying a different solvent, wherein up to five (5) different solvents may be connected to the system at any given time.

Experiment 9: Reverse Flow Elution v. Cross Flow Elution

Figure 19:
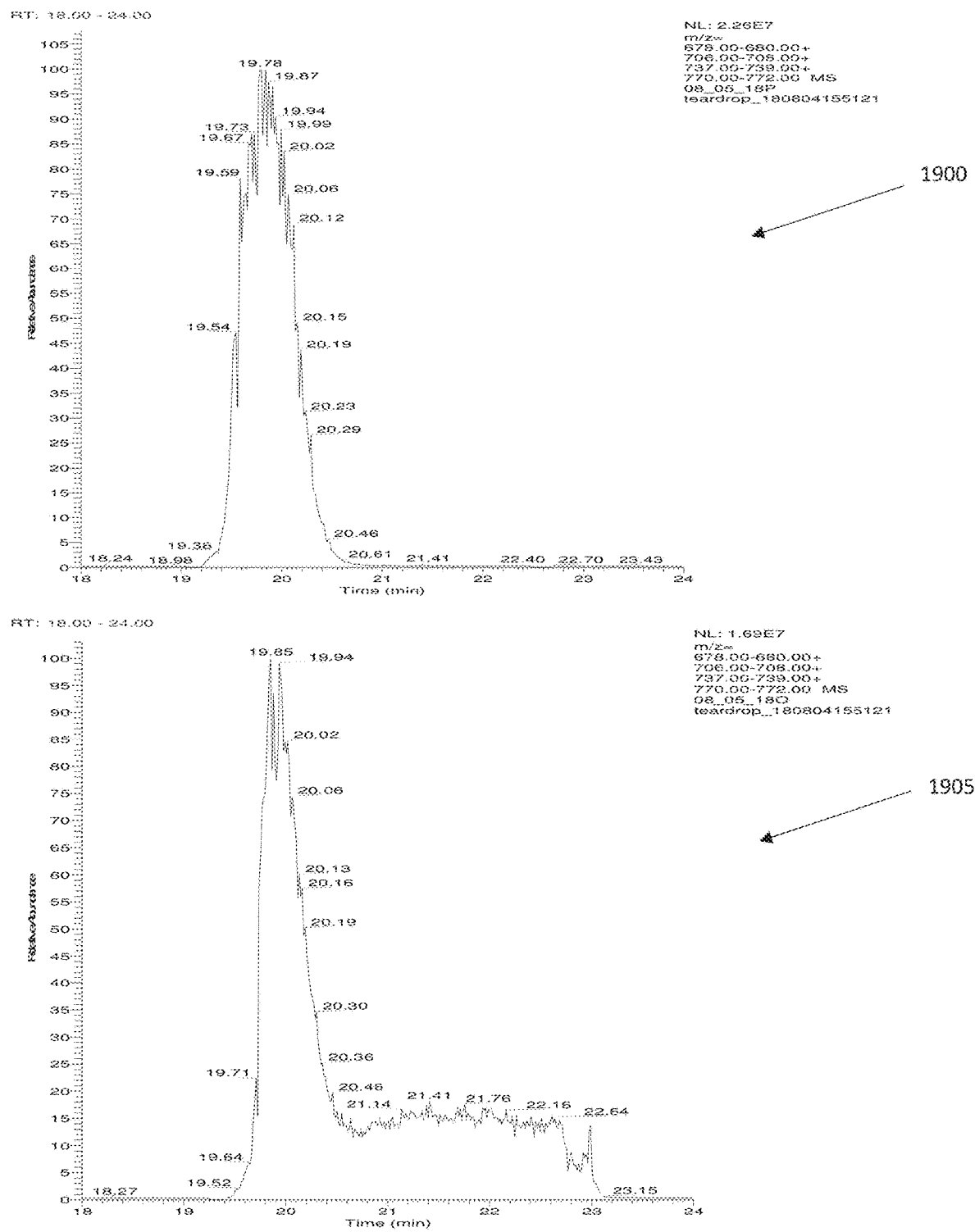
FIG. 19 is a set of graphs showing the increased efficacy of reverse flow elution as compared to cross flow elution.

A comparison was made between elution completed by reverse flow elution and cross flow elution while utilizing the molecular filtration device. The result of this elution comparison is shown in FIG. 19. As shown in FIG. 19, reverse flow elution creates a single sharp peak 1900, and cross flow elution creates a sharp peak followed by a tail end 1905. Both methods were performed using the same samples, solutions, pressures, and other conditions, and the only difference was the elution method. Specifically, reverse flow elution is conducted by preventing flow through a first upper port of the molecular filtration device and reversing flow of solution through a lower port of the molecular filtration device such that the sample is eluted out of the channel via the second upper port. The cross flow elution means that flow is prevented from passing through the lower port of the molecular filtration device, such that the sample is eluted through the second upper port.

Figure 20:
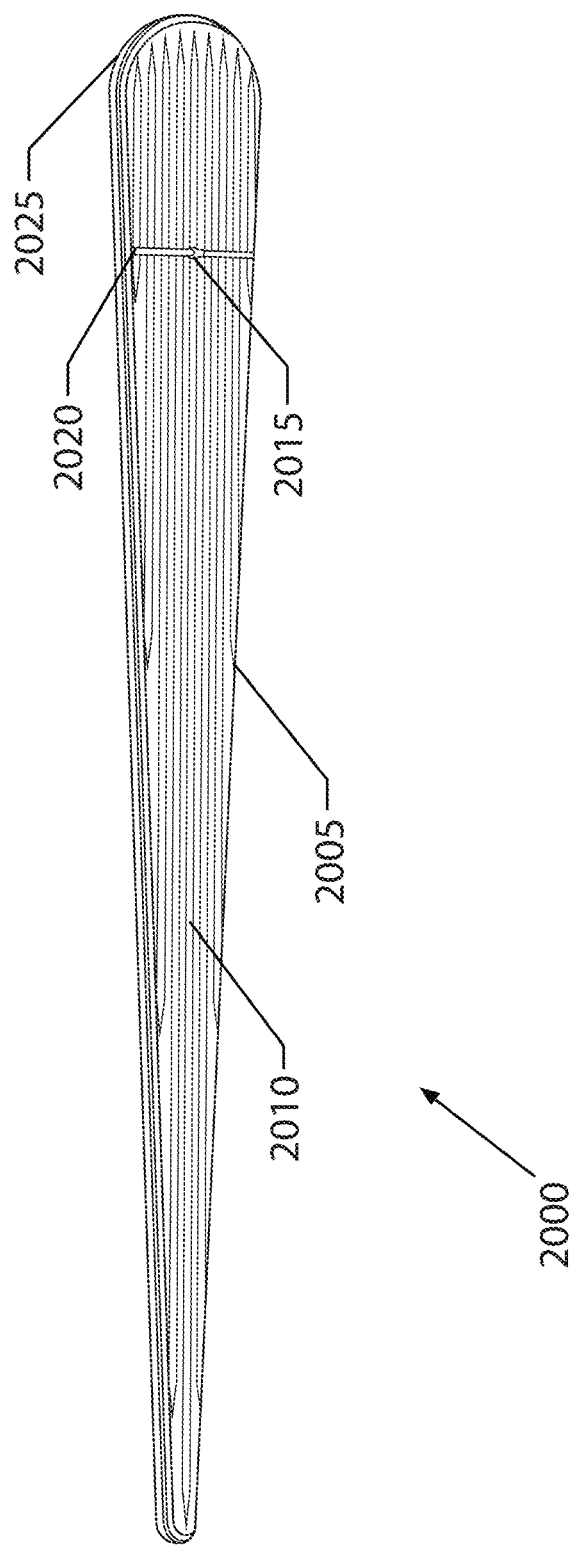
FIG. 20 is an illustration showing one embodiment of a grooved frit.

FIG. 20 is an illustration showing one embodiment of a grooved frit. As shown in FIG. 20, the grooved frit 2000 may comprise a main body 2005, a plurality of grooves 2010, a drain hole 2015, a transverse crossing lane 2020, and a perimeter lip 2025. The plurality of grooves 2010 may be parallel or substantially parallel and longitudinally traverse the main body 2005. The plurality of grooves 2010 may be varying lengths in order to substantially cover the surface of the main body 2005, despite contours in the shape of the main body 2005.

The drain hole 2015 may be located substantially anywhere on the main body 2005, but is preferably located on the transverse crossing lane 2020. In one embodiment, the drain hole 2015 may be at a center of said transverse crossing lane 2020. In one embodiment, the transverse crossing lane 2020 is substantially perpendicular to the plurality of grooves 2010.

As shown in FIG. 20, the main body 2005 may be teardrop shaped. In alternative embodiments, the main body 2005 may be oval, oblong, elongated rectangle shaped, or substantially any shape that may be received by a reservoir, as the term reservoir is used hereinabove.

The frit 2000 may be used to support a mesh, which may in turn support a membrane, as used hereinabove, in a molecular filtration apparatus. The plurality of grooves 2010 may increase directional flow and reduce the effects dead spots of solution flow along the frit 2000 and by extension, the membrane. This may be advantageous because it allows solution to flow relatively uniformly over the membrane and frit 2000, preventing the creation of uneven deposits of molecules on the membrane.

In one embodiment, the frit 2000 may be a substantially non-porous material. In one embodiment, the plurality of grooves 2010 may create drain lanes that are 0.005 inches (") wide and 0.005" deep, wherein the grooves extend outward from a surface of the frit 2000 at a 45 degree angle. The perimeter lip 2025 may be 0.005" wide and 0.005" deep. The transverse crossing lane 2020 may be 0.005" wide and 0.005" deep.

Figure 21:
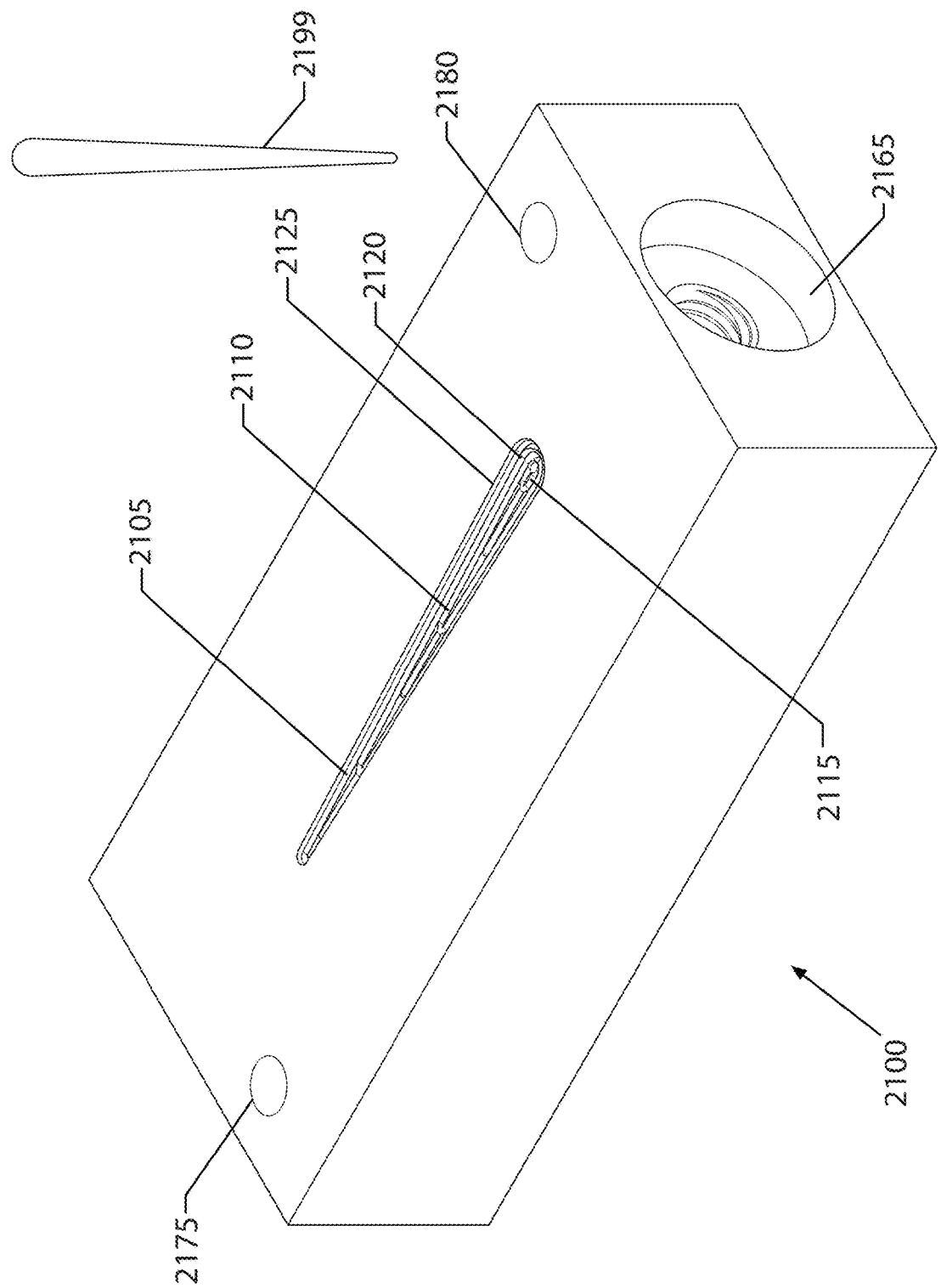
FIG. 21 is an illustration of a perspective view of one embodiment of a lower portion.

FIG. 21 is an illustration of a perspective view of one embodiment of a lower portion. As shown in FIG. 21, the lower portion 2100 may comprise a reservoir 2105, a plurality of grooves 2110, a drain hole 2115, a transverse crossing lane 2120, a perimeter lip 2125, a lower port 2165, and lower securing structures 2175, 2180.

The lower portion 2100 of FIG. 21 may be configured to have a substantially similar use and function as the lower portion 150 shown and described in FIG. 1, hereinabove. In some embodiments, the lower portion 2100 of FIG. 21 may be configured to replace the lower portion 150 of FIG. 1. The lower portion 2100 may be configured to work with or otherwise engage the upper portion 105, as shown and described in FIG. 1.

The plurality of grooves 2110 may be parallel or substantially parallel and longitudinally traverse a base of the reservoir 2105. The plurality of grooves 2110 may be of varying lengths such that the plurality of grooves may be configured to create a plurality of channels that are substantially similar in width and are distributed along the base of the reservoir 2105.

The transverse crossing lane 2120 may be substantially perpendicular to the plurality of grooves 2110, such that the transverse crossing lane 2120 may be configured to allow solution that travels along the channels created by the plurality of grooves 2110 to be consolidated. The transverse crossing lane 2120 may be positioned toward one end of the reservoir 2105. In one embodiment, the drain hole 2115 may be located on the transverse crossing lane 2120. Preferably, the drain hole 2115 may be located at a center portion of the transverse crossing lane 2120. The drain hole 2115 may be in fluid communication with the lower port 2165, such that solution may travel along the channels created by the plurality of grooves 2110, into the transverse crossing lane 2120, and through the drain hole 2115, such that the solution exits the lower portion 2100 through the lower port 2165.

The perimeter lip 2125, may be configured to be an indentation from a top surface of the lower portion 2100. The perimeter lip 2125 may be configured to receive a mesh 2199 or other supporting structure, that may be configured to provide support to a membrane at rest on the top surface of the lower portion 2100. The mesh 2199 is preferably porous and may allow solution to flow through it relatively unobstructed. The mesh 2199, when in at an rest state, is preferably slightly larger in surface area than the perimeter lip 2125, such that the mesh 2199 may be flexed in order to engage the perimeter lip 2125. In this flexed state, the mesh 2199 may form a snug seal against the perimeter lip 2125, and provide support for the membrane. The mesh 2199 may be a laser cut 165×800 (0.0065" thick, 25 µm pore size) twill Dutch weave 316SS wire mesh.

The plurality of grooves 2110 may be used to support the mesh 2199, which may in turn support a membrane, as used hereinabove, in a molecular filtration apparatus. The plurality of grooves 2110 reduces the amount of dead space by directing flow of solution in the reservoir 2105 and by extension, the membrane. This may be advantageous because it allows solution to flow relatively uniformly over the membrane, preventing the creation of uneven deposits of molecules on the membrane.

In one embodiment, the plurality of grooves 2110 may have a height that is equal to or slightly less than the height of the reservoir 2105. In some embodiments, the plurality of grooves 2110 may have a height such that the top of the plurality of grooves 2110 may be in line with the perimeter lip 2125.

Figure 22:
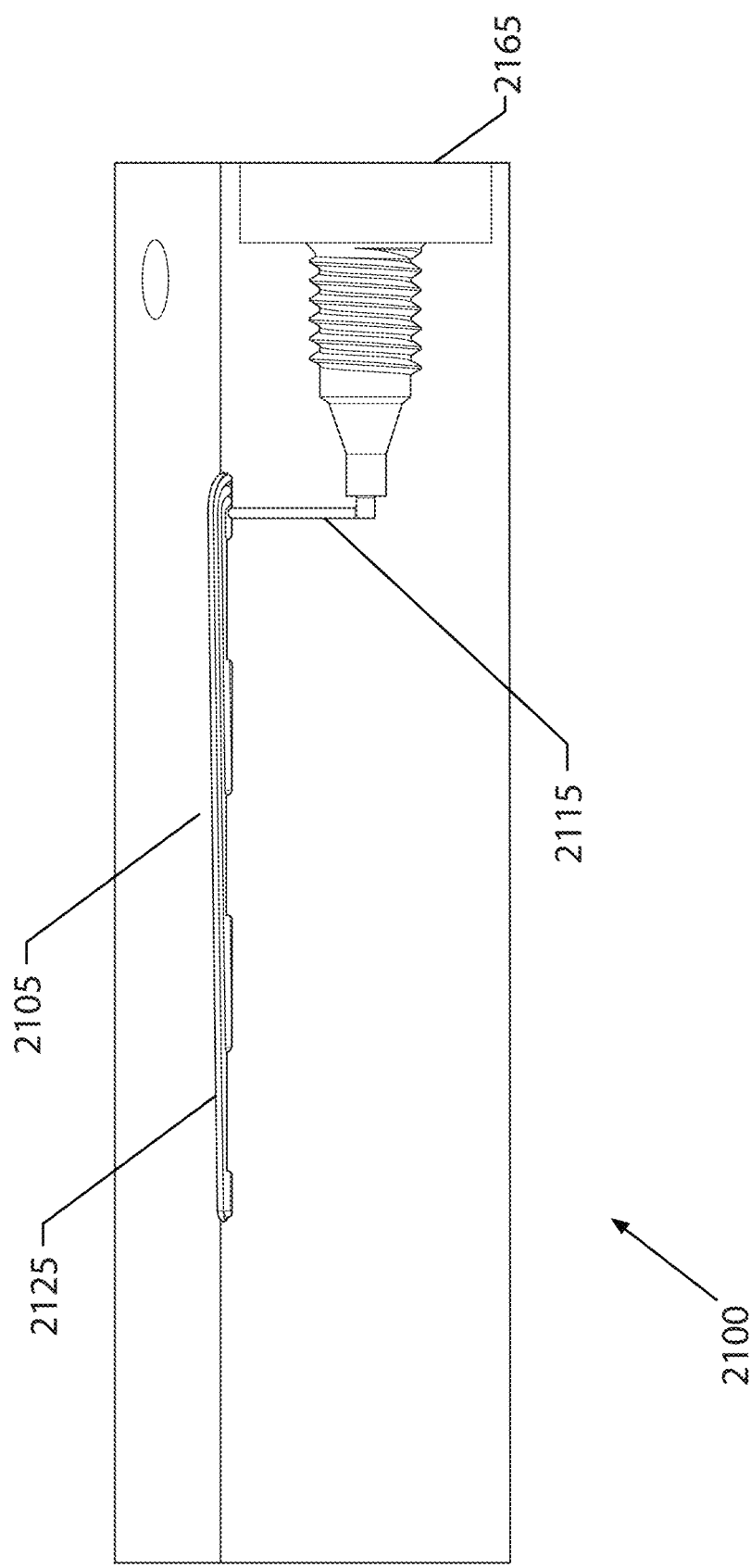
FIG. 22 is an illustration of a transparent side view of one embodiment of a lower portion of the molecular filtration device.

FIG. 22 is an illustration of a transparent side view of one embodiment of a lower portion of the molecular filtration device. As shown in FIG. 22, the lower portion 2100 may comprise a lower port 2165, perimeter lip 2125, drain port 2116, which may be connected to drain hole 2115, and reservoir 2105. The lower end of lower port 2165 may be configured to receive a lower flow device. The perimeter lip 2125 may be configured to receive the mesh 2199.

Figure 23:
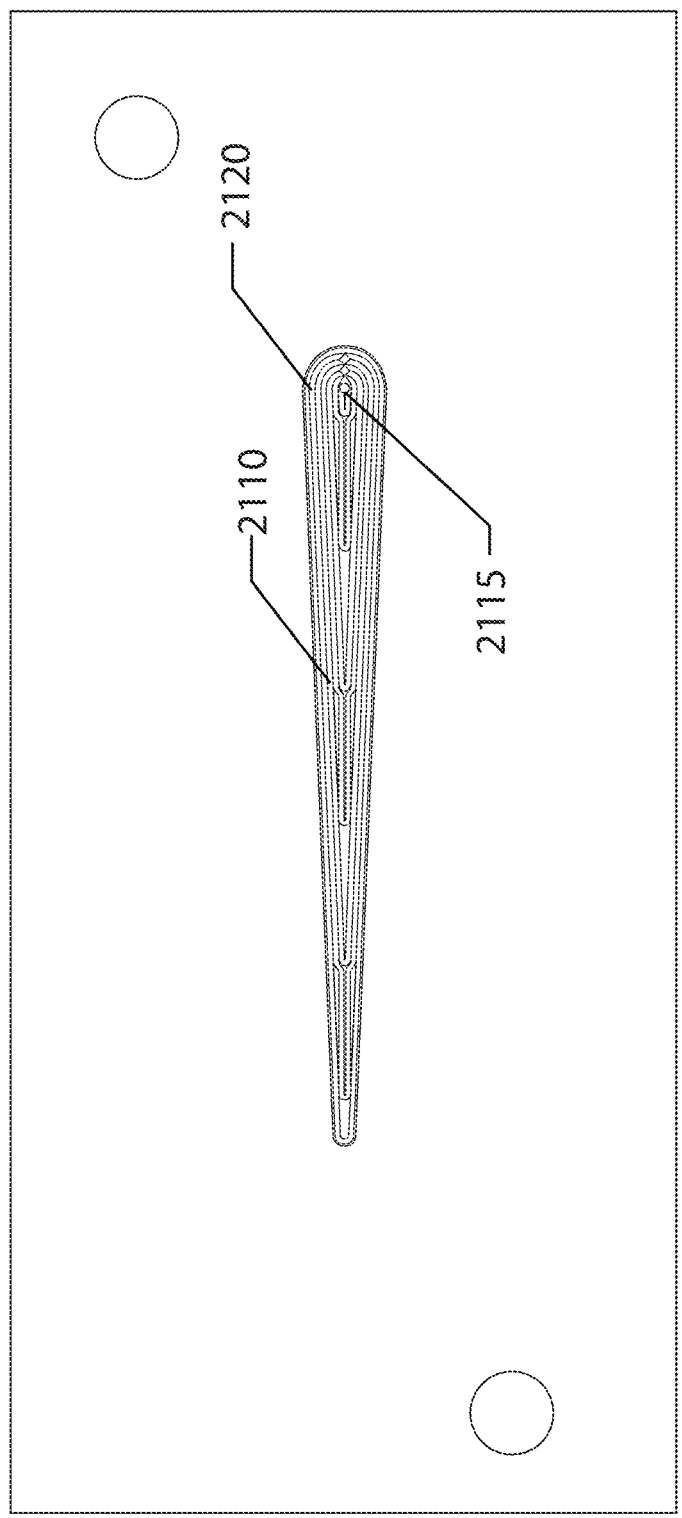
FIG. 23 is an illustration of a top view of the lower portion showing the plurality of grooves.

FIG. 23 is an illustration of a top view of the lower portion showing the plurality of grooves. As shown in FIG. 23, the lower portion 2100 may comprise the plurality of grooves 2110 arranged in such a configuration to match a channel forming cavity, such as the channel forming cavity 845 shown and described in FIG. 8B.

The foregoing description of the preferred embodiment has been presented for the purposes of illustration and description. While multiple embodiments are disclosed, still other embodiments will become apparent to those skilled in the art from the above detailed description. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those of ordinary skill in the art that various modifications and variations may be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:
1. A frit comprising:
a main body; and
a plurality of grooves;
wherein said main body is configured to be received by a reservoir;

wherein said reservoir is a part of a molecular filtration device that comprises an upper portion and a lower portion;

wherein said upper portion comprises two upper ports;

wherein said two upper ports comprise a first upper port and a second upper port;

wherein said first upper port is configured to receive a first upper flow device;

wherein said second upper port is configured to receive a second upper flow device;

wherein said lower portion comprises a lower port and said reservoir;

wherein said lower port is configured to receive a lower flow device;

wherein said upper portion comprises a channel forming lip;

wherein a channel forming cavity is formed by said channel forming lip when said upper portion and said lower portion engage one another;

wherein a lower sealing surface of said upper portion and an upper sealing surface of said lower portion are configured to receive a membrane; and wherein a channel is defined by said channel forming cavity and said membrane.

2. The frit of claim 1, wherein said plurality of grooves are parallel to one another and extend longitudinally across a top surface of said main body.

3. The frit of claim 1, further comprising a drain hole.

4. The frit of claim 3, further comprising a transverse crossing lane;

wherein said transverse crossing lane is perpendicular to said plurality of grooves.

5. The frit of claim 4, wherein said drain hole is located within said transverse crossing lane.

6. The frit of claim 5, wherein said drain hole is located at a center of said transverse crossing lane.

7. The frit of claim 1, further comprising a perimeter lip;

wherein said perimeter lip extends around a shape of said main body.

8. The frit of claim 1, wherein said main body is teardrop shaped.

9. The frit of claim 1, wherein said main body is elongated rectangle shaped.

10. A filtration component comprising:

a lower portion;

wherein said lower portion comprises a plurality of grooves in a reservoir of said lower portion;

wherein said lower portion is configured to be used with a molecular filtration device, which further comprises an upper portion;

wherein said upper portion comprises two upper ports;

wherein said two upper ports comprise a first upper port and a second upper port;

wherein said first upper port is configured to receive a first upper flow device;

wherein said second upper port is configured to receive a second upper flow device;

wherein said lower portion comprises a lower port and said reservoir;

wherein said lower port is configured to receive a lower flow device;

wherein said upper portion comprises a channel forming lip;

wherein a channel forming cavity is formed by said channel forming lip when said upper portion and said lower portion engage one another;

wherein a lower sealing surface of said upper portion and an upper sealing surface of said lower portion are configured to receive a membrane; and wherein a channel is defined by said channel forming cavity and said membrane.

11. The filtration component of claim 10, wherein said plurality of grooves extend longitudinally across said reservoir.

12. The frit of claim 11, wherein said plurality of grooves define a series of channels similar in width.

13. The filtration component of claim 10, further comprising a drain hole and drain port.

14. The filtration component of claim 13, further comprising a transverse crossing lane;

wherein said transverse crossing lane is perpendicular to said plurality of grooves.

15. The filtration component of claim 14, wherein said drain hole is located within said transverse crossing lane.

16. The filtration component of claim 15, wherein said drain hole is located at a center of said transverse crossing lane.

17. The filtration component of claim 10, wherein said reservoir is teardrop shaped.

18. The filtration component of claim 10, wherein said lower portion comprises a perimeter lip, wherein said perimeter lip is configured to receive a mesh.

* * * * *